United States Patent
Duque et al.

(10) Patent No.: US 10,194,908 B2
(45) Date of Patent: Feb. 5, 2019

(54) SURGICAL STAPLE CARTRIDGE WITH ENHANCED KNIFE CLEARANCE

(71) Applicant: Intuitive Surgical Operations, Inc., Sunnyvale, CA (US)

(72) Inventors: Grant Duque, San Jose, CA (US); Thomas N. McNamara, Sunnyvale, CA (US); Jeffrey A. Smith, Petaluma, CA (US); Bennie Thompson, San Carlos, CA (US); Ashley Wellman, Cupertino, CA (US); Donald Frank Wilson, Jr., Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 181 days.

(21) Appl. No.: 15/279,814

(22) Filed: Sep. 29, 2016

(65) Prior Publication Data

US 2017/0079651 A1    Mar. 23, 2017

Related U.S. Application Data

(63) Continuation of application No. 14/145,855, filed on Dec. 31, 2013, now Pat. No. 9,498,215.
(Continued)

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 34/25* (2016.02);
(Continued)

(58) Field of Classification Search
CPC . A61B 17/07207; A61B 17/072; A61B 34/30; A61B 34/37; A61B 50/36;
(Continued)

(56) References Cited

U.S. PATENT DOCUMENTS

| | | |
|---|---|---|
| 4,802,614 A | 2/1989 | Green et al. |
| 5,307,976 A | 5/1994 | Olson et al. |

(Continued)

FOREIGN PATENT DOCUMENTS

| | | |
|---|---|---|
| CN | 2751749 Y | 1/2006 |
| CN | 101966093 A | 2/2011 |

(Continued)

OTHER PUBLICATIONS

Extended European Search Report for Application No. 13867527.7, dated Jul. 19, 2016, 8 pages.
(Continued)

*Primary Examiner* — Robert Long
(74) *Attorney, Agent, or Firm* — Intuitive Surgical Operations, Inc.

(57) ABSTRACT

A surgical instrument having an elongated shaft having a shaft distal end and a shaft proximal end. An end effector is coupled to the shaft distal end and includes opposed jaws. A housing is included in one of the jaws, the housing having a housing proximal end, a housing distal end, an upper surface, a distal garage having lateral surfaces that extend above the upper surface, and a plurality of staple openings extending through the upper surface. A knife member is supported within the housing for movement distally. The knife member is moveable into a predetermined parked position such that a first portion of the cutting blade displaces below the upper surface and a second portion remains displaced above the upper surface. There is enough lateral clearance in the predetermined parked position between the
(Continued)

lateral faces and the second portion to accommodate a dislodged staple.

20 Claims, 22 Drawing Sheets

Related U.S. Application Data

(60) Provisional application No. 61/747,970, filed on Dec. 31, 2012.

(51) Int. Cl.
| | | |
|---|---|---|
| *A61B 34/30* | (2016.01) | |
| *A61B 50/13* | (2016.01) | |
| *A61B 50/33* | (2016.01) | |
| *A61B 34/00* | (2016.01) | |
| *A61B 34/37* | (2016.01) | |
| *A61B 17/00* | (2006.01) | |

(52) U.S. Cl.
CPC .............. *A61B 34/30* (2016.02); *A61B 34/37* (2016.02); *A61B 50/13* (2016.02); *A61B 50/33* (2016.02); *A61B 2017/00477* (2013.01); *A61B 2017/07228* (2013.01); *A61B 2017/07278* (2013.01); *A61B 2017/07285* (2013.01)

(58) Field of Classification Search
CPC ......... A61B 34/25; A61B 50/30; A61B 50/33; A61B 50/37; A61B 2017/00845; A61B 2017/07285; A61B 17/068; A61B 17/285; A61B 17/295
USPC ...................... 227/175.1–182.1; 606/75, 219
See application file for complete search history.

(56) References Cited

U.S. PATENT DOCUMENTS

| | | | |
|---|---|---|---|
| 5,433,721 A | 7/1995 | Hooven et al. | |
| 5,485,947 A | 1/1996 | Olson et al. | |
| 5,529,235 A | 6/1996 | Boiarski et al. | |
| 5,597,107 A | 1/1997 | Knodel et al. | |
| 5,632,432 A | 5/1997 | Schulze et al. | |
| 5,673,841 A | 10/1997 | Schulze et al. | |
| 5,752,644 A | 5/1998 | Bolanos et al. | |
| 5,762,255 A | 6/1998 | Chrisman et al. | |
| 5,810,240 A | 9/1998 | Robertson | |
| 5,816,471 A | 10/1998 | Plyley et al. | |
| 5,878,938 A | 3/1999 | Bittner et al. | |
| 6,010,054 A | 1/2000 | Johnson et al. | |
| 6,716,232 B1 | 4/2004 | Vidal et al. | |
| 6,843,403 B2 | 1/2005 | Whitman | |
| 7,055,730 B2 | 6/2006 | Ehrenfels et al. | |
| 7,134,587 B2 | 11/2006 | Schwemberger et al. | |
| 7,467,740 B2 | 12/2008 | Shelton et al. | |
| 7,604,151 B2 | 10/2009 | Hess et al. | |
| 7,641,093 B2 | 1/2010 | Doll et al. | |
| 7,726,537 B2 | 6/2010 | Olson et al. | |
| 7,918,230 B2 | 4/2011 | Whitman et al. | |
| 8,225,979 B2 * | 7/2012 | Farascioni ....... | A61B 17/07207 227/175.2 |
| 8,276,594 B2 | 10/2012 | Shah | |
| 8,286,850 B2 | 10/2012 | Viola | |
| 8,365,975 B1 | 2/2013 | Manoux et al. | |
| 8,657,177 B2 | 2/2014 | Scirica et al. | |
| 8,746,533 B2 | 6/2014 | Whitman et al. | |
| 8,991,678 B2 | 3/2015 | Wellman et al. | |
| 9,498,215 B2 | 11/2016 | Duque et al. | |
| 9,757,125 B2 | 9/2017 | Wellman et al. | |
| 9,924,941 B2 | 3/2018 | Burbank et al. | |
| 2003/0055424 A1 | 3/2003 | Ciarrocca | |
| 2004/0094597 A1 | 5/2004 | Whitman et al. | |
| 2005/0103819 A1 | 5/2005 | Racenet et al. | |
| 2006/0273135 A1 | 12/2006 | Beetel | |
| 2007/0023477 A1 | 2/2007 | Whitman et al. | |
| 2007/0095877 A1 | 5/2007 | Racenet et al. | |
| 2007/0123889 A1 | 5/2007 | Malandain et al. | |
| 2007/0175950 A1 | 8/2007 | Shelton et al. | |
| 2008/0027472 A1 | 1/2008 | Nielsen et al. | |
| 2008/0237298 A1 | 10/2008 | Schall et al. | |
| 2008/0308601 A1 | 12/2008 | Timm et al. | |
| 2009/0302093 A1 | 12/2009 | Kasvikis | |
| 2010/0065604 A1 | 3/2010 | Weng | |
| 2010/0072257 A1 * | 3/2010 | Farascioni ....... | A61B 17/07207 227/180.1 |
| 2010/0213240 A1 | 8/2010 | Kostrzewski | |
| 2010/0256634 A1 | 10/2010 | Voegele et al. | |
| 2010/0292691 A1 | 11/2010 | Brogna | |
| 2010/0320252 A1 | 12/2010 | Viola et al. | |
| 2011/0068147 A1 | 3/2011 | Racenet et al. | |
| 2011/0226837 A1 | 9/2011 | Baxter, III et al. | |
| 2011/0315741 A1 * | 12/2011 | Nelson ................. | A61B 17/068 227/176.1 |
| 2012/0248167 A1 | 10/2012 | Flanagan et al. | |
| 2012/0273551 A1 | 11/2012 | Shelton, IV et al. | |
| 2012/0305626 A1 | 12/2012 | Stopek | |
| 2012/0310255 A1 | 12/2012 | Brisson et al. | |
| 2013/0037597 A1 | 2/2013 | Katre et al. | |
| 2013/0098966 A1 | 4/2013 | Kostrzewski et al. | |
| 2013/0105545 A1 | 5/2013 | Burbank | |
| 2013/0105552 A1 | 5/2013 | Weir et al. | |
| 2013/0123822 A1 * | 5/2013 | Wellman ........... | A61B 17/07207 606/170 |
| 2013/0334284 A1 | 12/2013 | Swayze et al. | |
| 2014/0103093 A1 * | 4/2014 | Koch, Jr. ......... | A61B 17/07207 227/180.1 |
| 2014/0183244 A1 | 7/2014 | Duque et al. | |
| 2014/0239046 A1 * | 8/2014 | Milliman ......... | A61B 17/07292 227/180.1 |
| 2015/0230794 A1 | 8/2015 | Wellman et al. | |
| 2017/0333037 A1 * | 11/2017 | Wellman ......... | A61B 17/07207 |
| 2018/0168572 A1 | 6/2018 | Burbank | |

FOREIGN PATENT DOCUMENTS

| | | |
|---|---|---|
| CN | 102178552 A | 9/2011 |
| EP | 1813201 A1 | 8/2007 |
| EP | 2245993 A2 | 11/2010 |
| EP | 1977701 B1 | 12/2011 |
| EP | 2436319 A2 | 4/2012 |
| JP | H08336540 A | 12/1996 |
| JP | 2004305741 A | 11/2004 |
| JP | 2005511131 A | 4/2005 |
| JP | 2007216012 A | 8/2007 |
| JP | 2007229448 A | 9/2007 |
| JP | 2010240419 A | 10/2010 |
| JP | 2011509715 A | 3/2011 |
| WO | WO-2006124388 A1 | 11/2006 |
| WO | WO-2012112249 A1 | 8/2012 |

OTHER PUBLICATIONS

Extended European Search Report for Application No. EP12850096.4, dated Jun. 25, 2015, 8 pages.
Extended European Search Report for Application No. EP20120844202, dated Jun. 12, 2015, 10 pages.
International Search Report and Written Opinion for Application No. PCT/US13/78549, dated Apr. 16, 2014, 12 pages.
International Search Report and Written Opinion for Application No. PCT/US2012/062302 dated Feb. 26, 2013, 10 pages.
International Search Report and Written Opinion for Application No. PCT/US2012/062305, dated Feb. 26, 2013, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

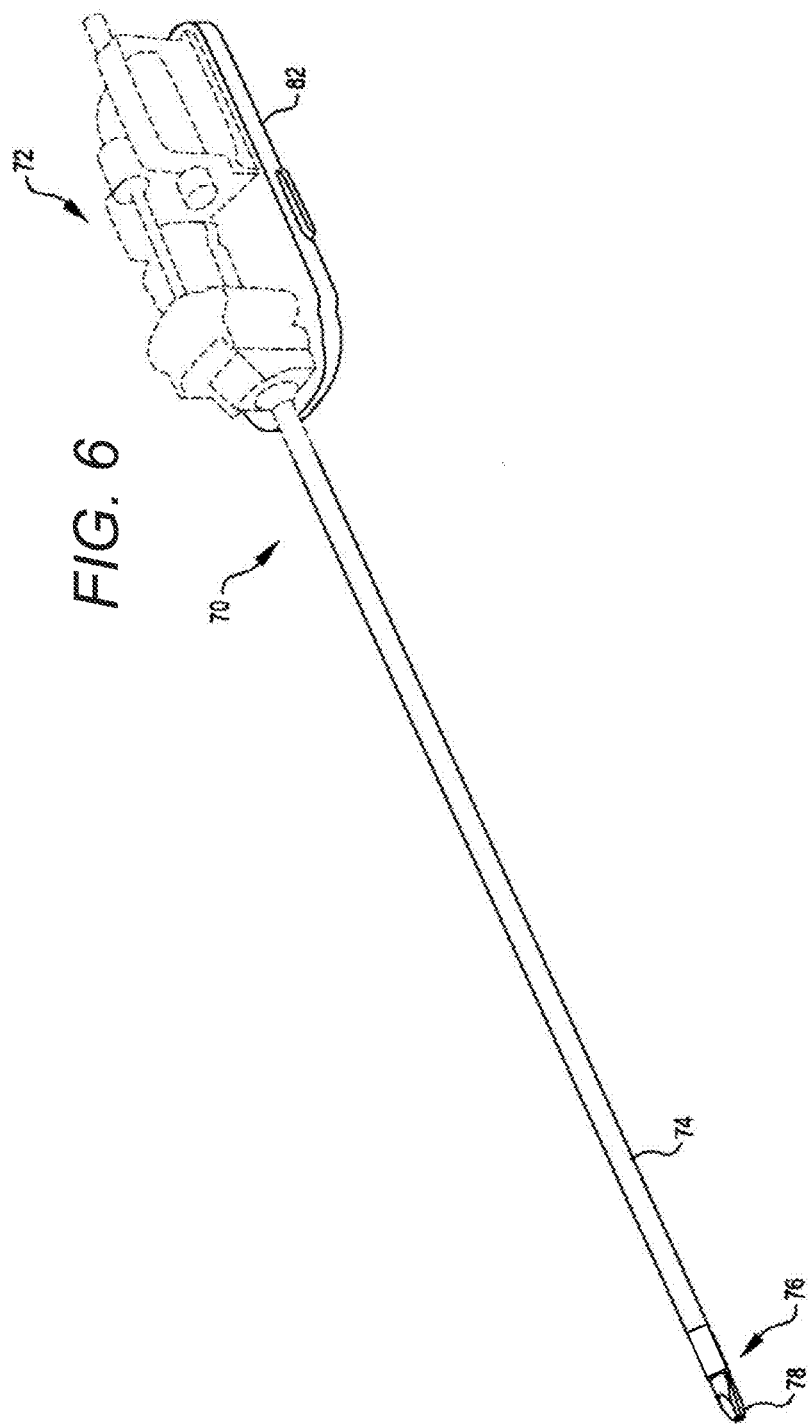

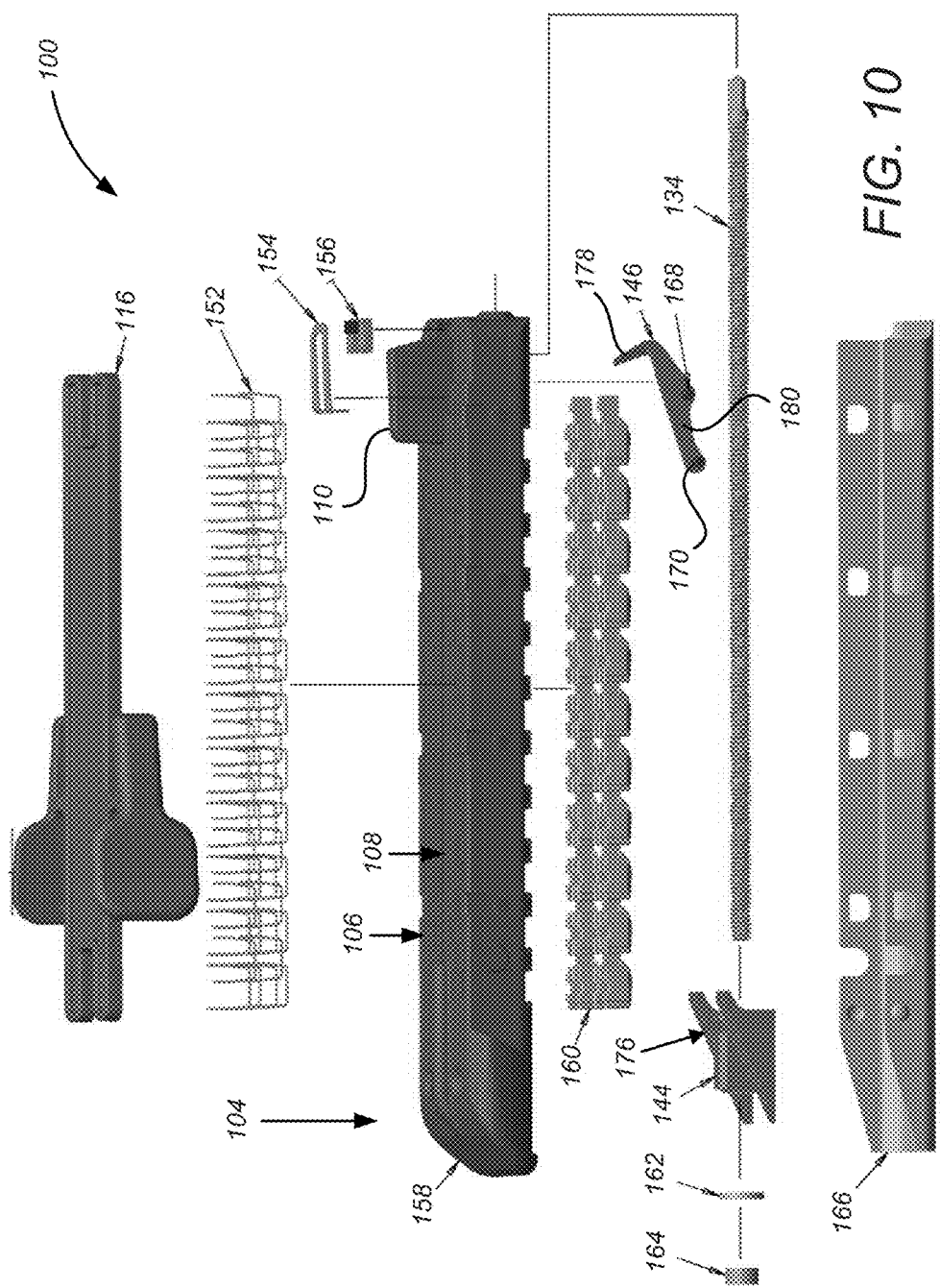

FIG. 15A
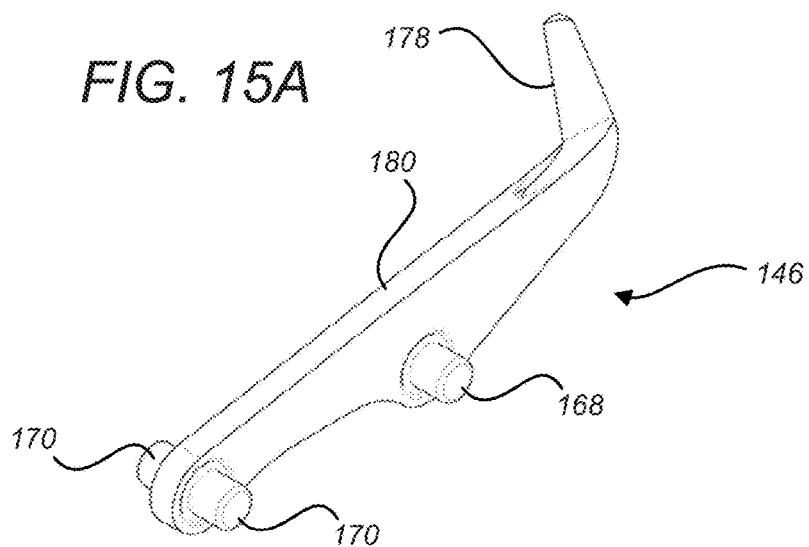
FIG. 15B
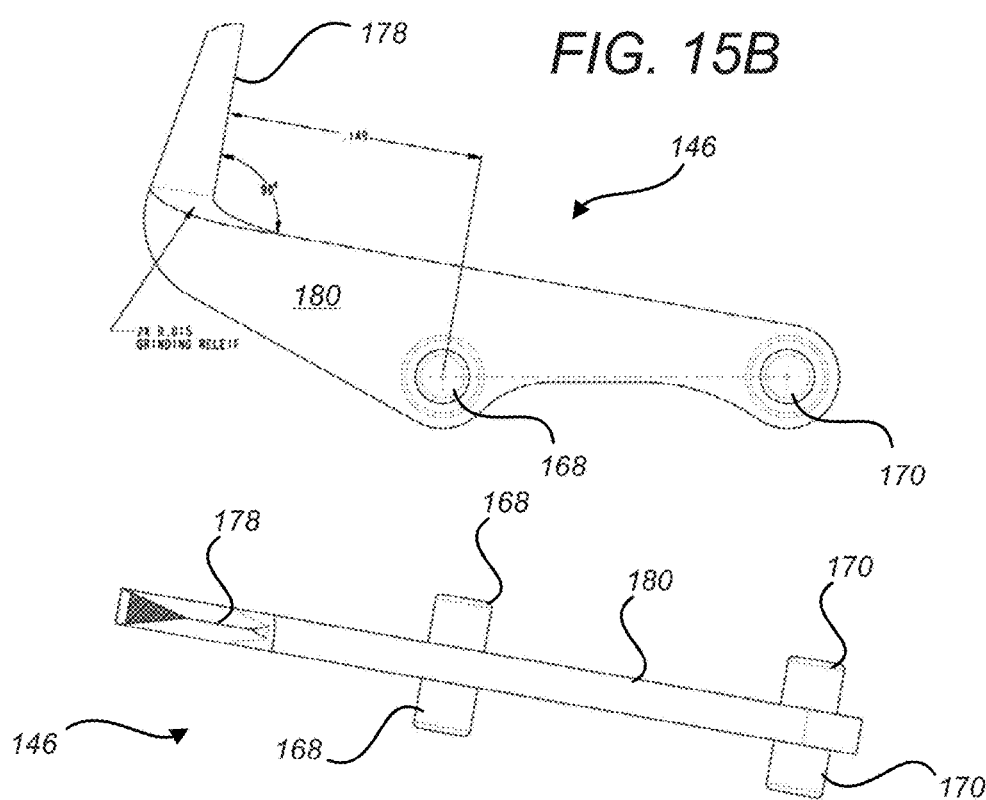
FIG. 15C

SURGICAL STAPLE CARTRIDGE WITH ENHANCED KNIFE CLEARANCE

CROSS REFERENCE TO RELATED APPLICATION DATA

The present application is a Continuation of U.S. application Ser. No. 14/145,855 filed Dec. 31, 2013 (Allowed); which claims the benefit of U.S. Provisional Appln No. 61/747,970 filed Dec. 31, 2012; each of which is incorporated herein by reference in its entirety for all purposes.

BACKGROUND OF THE INVENTION

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting instruments, including known surgical staplers, have opposing jaws that clamp tissue and an articulated knife to cut the clamped tissue.

Surgical clamping and cutting instruments are often deployed into restrictive body cavities (e.g., through a cannula to inside the pelvis). Accordingly, it is desirable for a surgical clamping and cutting instrument to be both compact and maneuverable for best access to and visibility of the surgical site. Known surgical clamping and cutting instruments, however, may fail to be both compact and maneuverable. For example, known surgical staplers may lack maneuverability with respect to multiple degrees of freedom (e.g., Roll, Pitch, and Yaw) and associated desired ranges of motion. Typically, known surgical staplers have a smaller range of Pitch motion than desirable and no Yaw motion.

Additionally, surgical clamping and cutting instruments can sometimes fail to fully actuate (e.g., due to a hard obstacle blocking the knife path). In such an event, it is desirable that the knife blade not be in a position that may represent a hazard with respect to removal of the surgical instrument from the surgical site. Known surgical clamping and cutting instruments, however, may fail to avoid the potential knife hazard and at the same time be compact and maneuverable.

Thus, there is believed to be a need for improved surgical clamping and cutting instruments and related methods. Such surgical clamping and cutting instruments should be compact and maneuverable, and employ a knife that does not represent a hazard with respect to removal of the surgical instrument from the surgical site when the surgical instrument fails to fully actuate.

BRIEF SUMMARY OF THE INVENTION

Improved surgical clamping and cutting instruments (e.g., surgical staplers, and electrosurgical vessel sealing devices) and related methods are disclosed. Surgical clamping and cutting instruments described herein employ a proximal to distal knife movement, thereby orienting the knife to greatly reduce the likelihood of unintentionally cutting tissue while removing the surgical instrument from the surgical site in the event that the surgical instrument fails to fully actuate. Surgical clamping and cutting instruments described herein locate the knife and associated drive mechanism distal to the wrist of the surgical instrument, thereby permitting the use of a high motion wrist to provide high maneuverability. And surgical clamping and cutting instruments described herein employ relative movement between the drive mechanism and the knife, thereby reducing the length of the surgical instrument. Further, surgical clamping and cutting instruments described herein employ unique features to prevent dislodged staples, or staples from prior surgeries, from jamming the knife in an exposed position with other portions of the instrument. Thus, preventing inadvertent injury associated with an unintentionally exposed knife blade.

Thus, in one aspect, a method of articulating a cutting blade in a surgical instrument is disclosed. The method includes supporting a knife member having a cutting blade within a housing of the instrument. The housing has an upper surface with a plurality of staple openings, a proximal end, and a distal end. The knife member is moved distally from the proximal end of the housing to the distal end of the housing such that the knife member is exposed and above the upper surface during movement of the knife member. A plurality of staples exit the upper surface during movement the knife member. The knife member is placed into a predetermined parked position at the distal end of the housing such that a first portion of the knife member displaces below the upper surface, while a second portion remains displaced above the upper surface. The second portion is laterally faced by a garage that extends above the upper surface. There is enough lateral clearance in the predetermined parked position between the garage and the second portion to accommodate a dislodged staple.

In another aspect, a surgical instrument is disclosed. The surgical instrument includes an elongated shaft having a shaft distal end and a shaft proximal end and an end effector coupled to the shaft distal end and including opposed jaws. A housing is included in one of the jaws, the housing including a housing proximal end, a housing distal end, an upper surface extending between the housing proximal and distal ends, a distal garage having lateral surfaces that extend above the upper surface, and a plurality of staple openings extending through the upper surface. A knife member is supported within the housing for movement distally, the knife member having a cutting blade configured to cut when the knife member is moved distally. The knife member is moveable into a predetermined parked position at the distal end of the housing such that a first portion of the cutting blade displaces below the upper surface and a second portion remains displaced above the upper surface. The second portion is laterally faced by the lateral surfaces of the garage. There is enough lateral clearance in the predetermined parked position between the lateral faces and the second portion to accommodate a dislodged staple.

In another aspect, a demountably attachable cartridge of a surgical instrument is disclosed. The cartridge includes a housing demountably attachable to an end effector of the surgical instrument. The housing includes a housing proximal end, a housing distal end, an upper surface extending between the housing proximal and distal ends, a distal garage having lateral surfaces that extend above the upper surface, and a plurality of staple openings extending through the upper surface. A knife member is supported within the housing for movement distally, the knife member having a cutting blade configured to cut when the knife member is moved distally. The knife member is moveable into a predetermined parked position at the distal end of the housing such that a first portion of the cutting blade displaces below the upper surface and a second portion remains displaced above the upper surface. The second portion is laterally faced by the lateral faces of the garage. There is enough lateral clearance in the predetermined parked position between the lateral faces and the second portion to accommodate a dislodged staple.

In many embodiments, the second portion includes a cutting tip of the cutting blade.

In many embodiments, the garage has lateral surfaces that face the cutting tip of the blade in the predetermined parked position.

In many embodiments, the cutting tip of the blade is displaced below the lateral surfaces in the predetermined parked position.

In many embodiments, the knife member is carried by a drive member.

In many embodiments, in the predetermined parked position the drive member is fully displaced within the distal end of the housing.

In many embodiments, the second portion of the cutting blade is laterally protected by the garage while in the predetermined parked position.

In many embodiments, during placement of the knife member into the predetermined parked position, a staple of the plurality of staples is dragged at least partially into the garage by the knife member. The staple can remain between the knife member and lateral surfaces of the garage while in the knife member is in the predetermined parked position or become ejected by collision with at least one staple ejection surface of the garage while placing the knife member into the predetermined parked position.

In many embodiments, the garage includes at least one staple ejecting surface.

In many embodiments, the at least one staple ejecting surface is transverse to the diverging lateral faces.

In many embodiments, the at least one staple ejecting surface is non-parallel to the upper surface.

In many embodiments, the at least one staple ejecting surface is at an angle ranging from 30-60° with respect to the upper surface.

In many embodiments, the predetermined parked position the drive member is fully displaced within the distal end of the housing.

In many embodiments, the lateral faces diverge to form a notch.

In many embodiments, the lateral faces diverge at an angle ranging from 25-45°.

In many embodiments, in the predetermined parked position, the lateral faces are spaced more than the maximum diameter of the staple wire e.g., 0.25 mm away from the second portion of the knife member.

BRIEF DESCRIPTION OF THE DRAWINGS

FIG. 6 is a perspective view of a robotic surgery tool that includes an end effector having opposed clamping jaws, in accordance with many embodiments.

FIG. 10 is an exploded perspective view illustrating components of the cartridge of FIG. 7.

FIG. 15A is a perspective view of a knife member of the cartridge of FIG. 7.

FIG. 15B is a side view of the knife member of the cartridge of FIG. 7.

FIG. 15C is a plan view of the knife member of the cartridge of FIG. 7.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
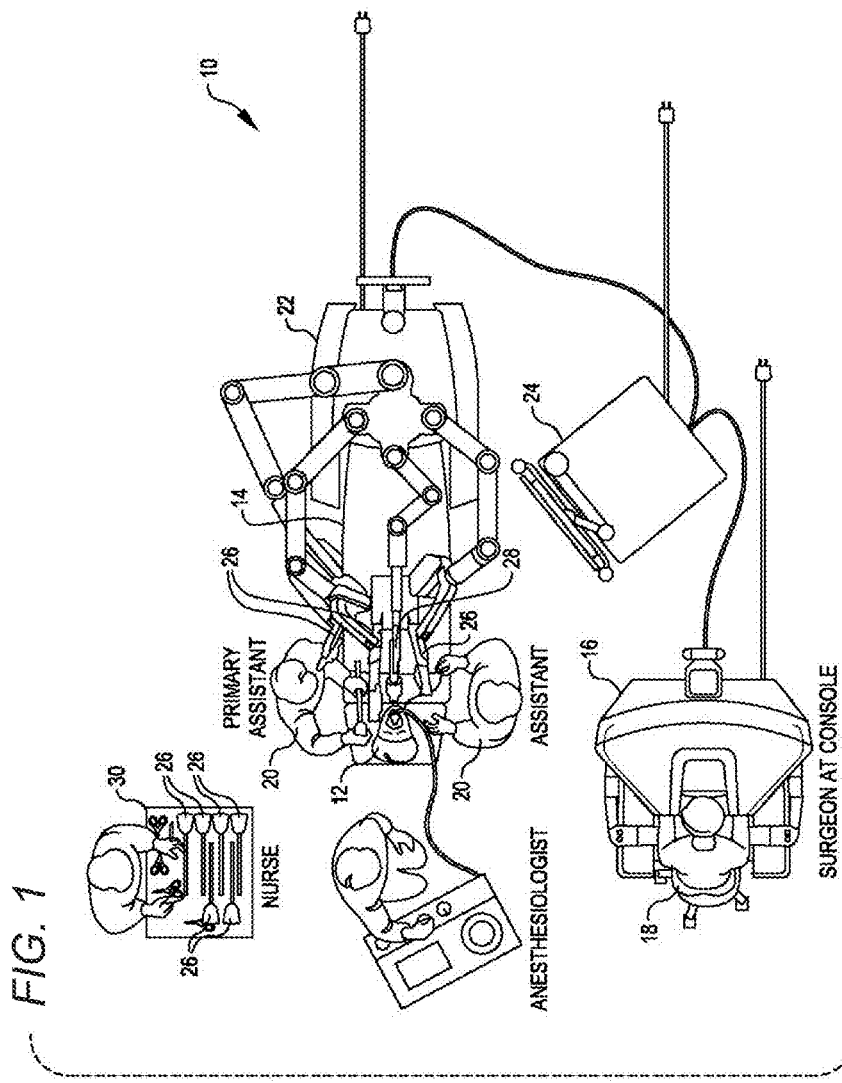
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
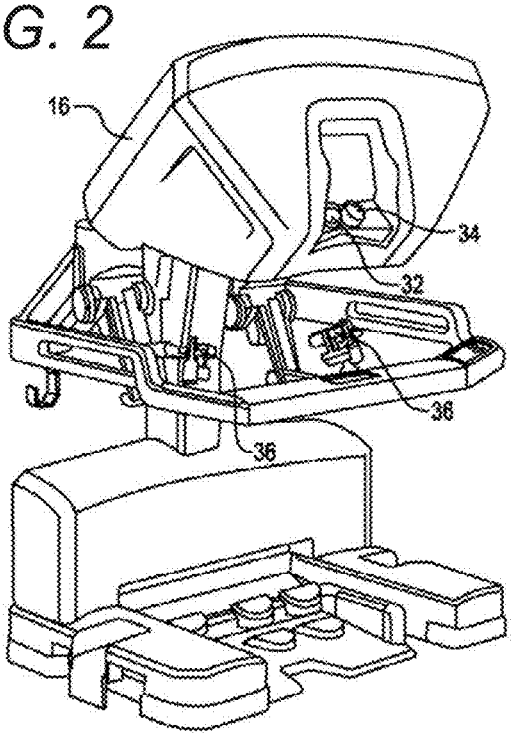
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
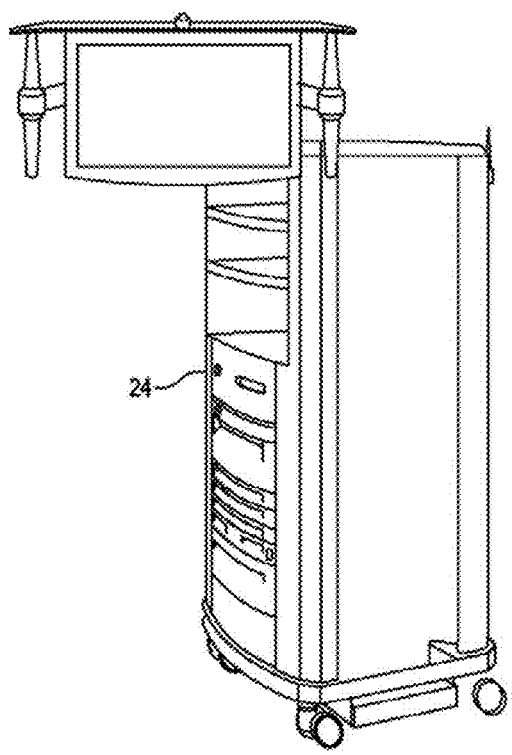
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
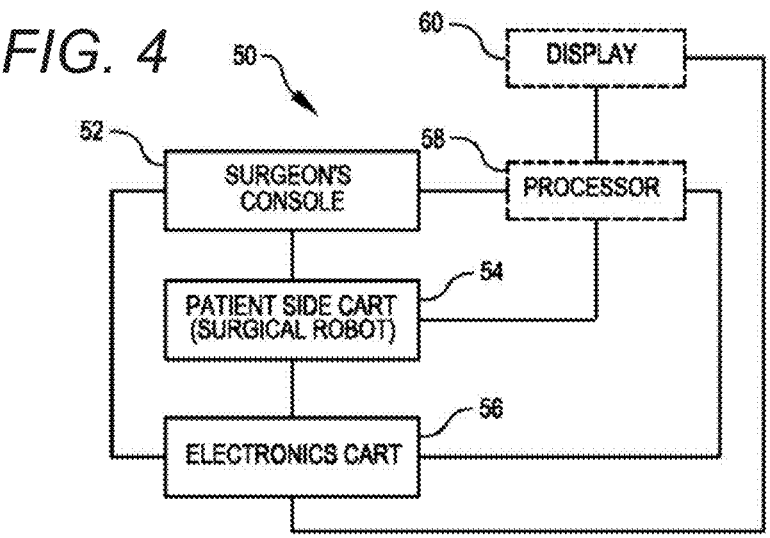
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
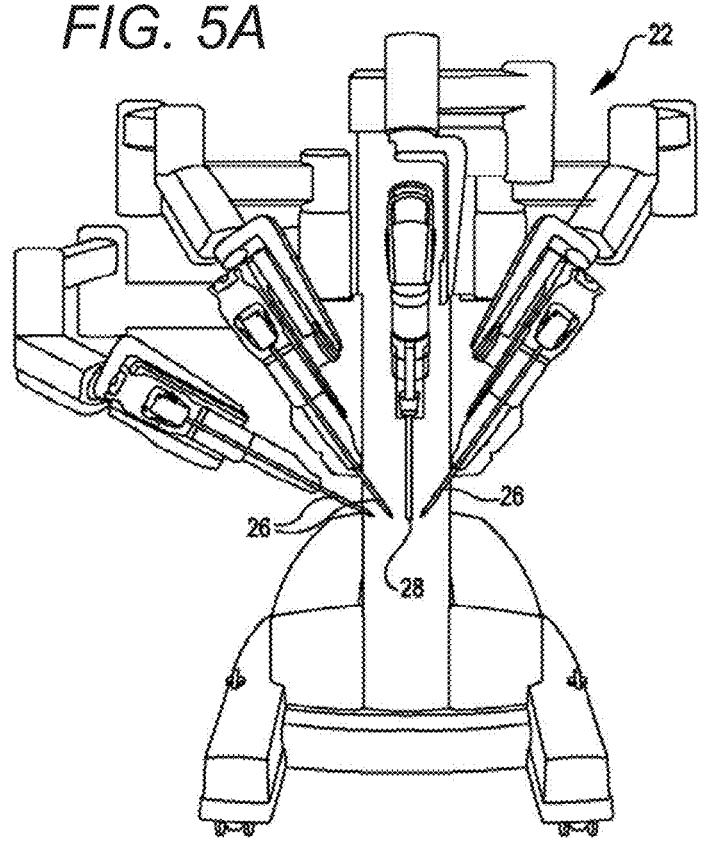
FIG. 5A is a front view of a patient side cart (surgical robot) of a robotic surgery system, in accordance with many embodiments.
Figure 5B:
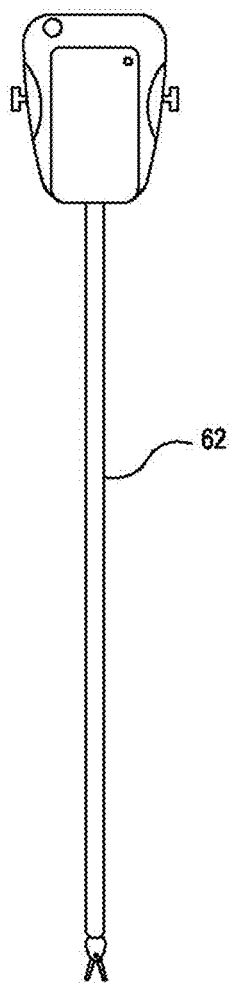
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Tissue Gripping End Effectors

FIG. 6 shows a surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Linear Stapling and Cutting Surgical Instruments

Figure 7:
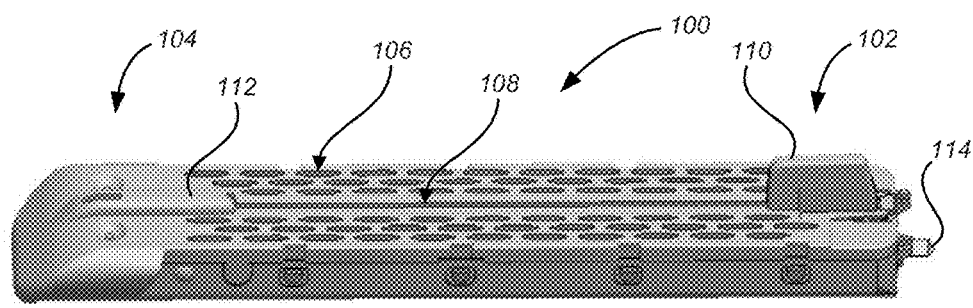
FIG. 7 is a perspective view of a demountably attachable cartridge of a linear stapling and cutting surgical instrument having six rows of staples, in accordance with many embodiments.
Figure 8:
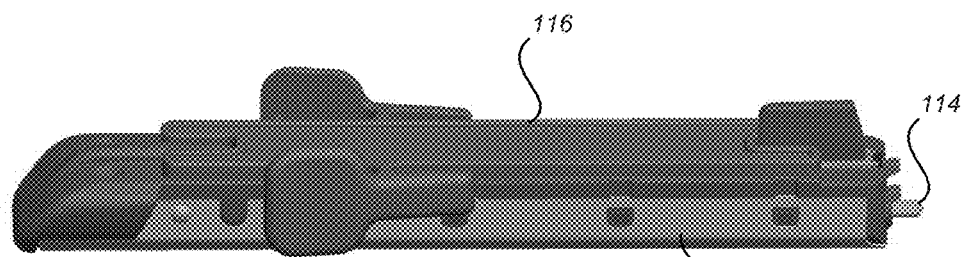
FIG. 8 is a perspective view of the cartridge of FIG. 7 and an attached staple retainer, in accordance with many embodiments.

FIG. 7 shows a demountably attachable cartridge 100 of a linear stapling and cutting surgical instrument, in accordance with many embodiments. The cartridge 100 is configured to removably attach to a jaw of an end effector. The cartridge has a proximal end 102 that is attached to the jaw of the end effector and a distal end 104 disposed at a corresponding distal end of the jaw of the end effector. The cartridge 100 includes six rows of staple openings 106, a longitudinal slot 108, a proximal knife garage 110, a distal knife garage 112, and a rotational input 114. In many embodiments, a staple is disposed in each of the staple openings for deployment there from. The longitudinal slot 108 accommodates a cutting blade of a knife member (not shown) extending there from as the knife member is moved from the proximal knife garage 110 to the distal knife garage 112. In operation, the staples are deployed starting at the cartridge proximal end 102 and proceeding to the cartridge distal end 104. The cutting blade is moved to trail the stapling of the tissue to ensure that only fully stapled tissue is cut. FIG. 8 shows the cartridge 100 with an attached staple retainer 116, which is removed prior to using the cartridge 100.

Figure 9:
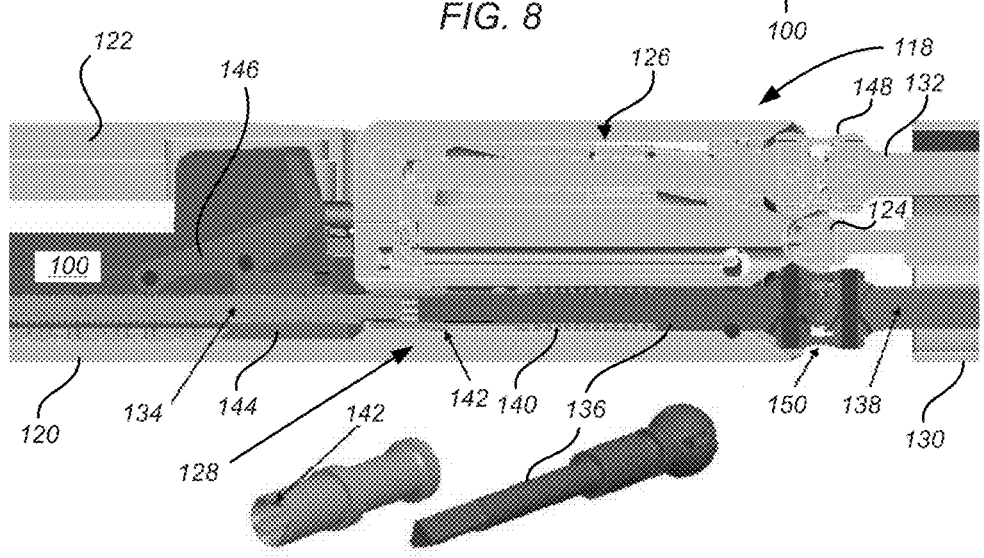
FIG. 9 is a cross-sectional view showing attachment details between the cartridge of FIG. 7 and an end effector assembly, in accordance with many embodiments.

FIG. 9 is a cross-sectional view showing details of the attachment of the cartridge 100 to an end effector 118, in accordance with many embodiments. The end effector 118 includes a lower jaw 120, an upper jaw 122, a two degree of freedom wrist 124, a rotationally-driven clamping mechanism 126, and a spring loaded coupling 128. The lower jaw 120 is configured to accommodate and support the cartridge 100, as well as position the cartridge 100 relative to the spring loaded coupling 128. The upper jaw 122 is pivotally coupled with the lower jaw 120 to articulate relative to the lower jaw 120 to clamp tissue. The upper jaw 122 includes staple forming recesses configured and positioned relative to the staple openings 106 to form the staples into a "B" shape upon deployment of the staples.

The two degree of freedom wrist 124 provides for attachment of the end effector 118 to an elongated instrument shaft 130 for articulation of the end effector 118 about two orthogonal axes relative to the instrument shaft 130. Details of a suitable two degree of freedom wrist that can be used are disclosed in U.S. application Ser. No. 12/945,748, entitled "SURGICAL TOOL WITH A TWO DEGREE OF FREEDOM WRIST," filed Nov. 12, 2010 now U.S. Pat. No. 8,852,174 issued on Oct. 7, 2014, the full disclosure of which is hereby incorporated herein by reference.

The rotationally-driven clamping mechanism 126 actuates the upper jaw 122 relative to the lower jaw 120 to securely clamp tissue between the upper and lower jaws. The clamping mechanism 126 is rotationally driven by a first drive shaft 132 disposed internal to the instrument shaft 130. Details of a suitable rotationally-driven clamping mechanism that can be used are disclosed in U.S. application Ser. No. 12/945,541, entitled "END EFFECTOR WITH REDUNDANT CLOSING MECHANISMS," filed Nov. 12, 2010, now U.S. Pat. No. 8,876,857 issued on Nov. 4, 2014, the full disclosure of which is hereby incorporated herein by reference.

The spring-loaded coupling 128 rotationally couples a lead screw 134 of the cartridge 100 with an extension shaft 136, which is driven by a second drive shaft 138 disposed internal to the instrument shaft 130. The spring-loaded coupling 128 includes a coil spring 140 and a coupling fitting 142. In the embodiment shown, the coupling fitting 142 employs a three-lobe spline receptacle that interfaces with three-sided external surfaces of the rotational input 114 and of the extension shaft 136. The spring-loaded coupling 142 accommodates angular misalignment of the three-lobe spline that might occur when cartridge 100 is installed into end effector 118. The spring-loaded coupling 142 fully engages the three-lobe spline when rotated into angular alignment. Rotation of the lead screw 134 is used to translate a drive member 144 of the cartridge 100. The resulting motion of the drive member 144 is used to deploy the staples and to distally advance a knife member 146 of the cartridge 100 to cut the clamped tissue down the center of the rows of deployed staples.

The end effector 118 includes a first universal joint assembly 148 and a second universal joint assembly 150. The first universal joint assembly 148 rotationally couples the clamping mechanism 126 to the first drive shaft 132. The second universal joint assembly 150 rotationally couples the extension shaft 136 to the second drive shaft 138. Each of the first and second universal joint assemblies 148, 150 is configured to transmit torque through a range of angles suitable to the range of Pitch and Yaw of the end effector 118 relative to the instrument shaft 130. Details of a suitable universal joint assembly that can be used are disclosed in U.S. application Ser. No. 12/945,740, entitled "DOUBLE UNIVERSAL JOINT," filed Nov. 12, 2010, the full disclosure of which is hereby incorporated herein by reference.

The first and second drive shafts 132, 138 are disposed offset to the centerline of the instrument shaft 130, which may be independently rotated. Details of a suitable drive mechanism that can be used to actuate the first and second drive shafts 132, 138 are disclosed in U.S. application Ser. No. 12/945,461, entitled "MOTOR INTERFACE FOR PARALLEL DRIVE SHAFTS WITHIN AN INDEPENDENTLY ROTATING MEMBER," filed Nov. 12, 2010, now U.S. Pat. No. 8,640,788 issued on Feb. 4, 2014, the full disclosure of which is hereby incorporated herein by reference.

FIG. 10 is an exploded perspective view illustrating components of the cartridge 100. The illustrated components include the retainer 116, 66 staples 152, a printed circuit assembly (PCA) spring 154, a PCA 156, a cartridge body 158, 22 staple pushers 160, the knife member 146, the lead screw 134, the drive member 144, a thrust washer 162, a lead screw nut 164, and a cover 166. The cartridge body 158 has the 66 staple openings 106 arranged in 6 rows, with 3 rows of the staple openings 106 being disposed on each side of the longitudinal slot 108. The retainer 116 is removably attachable to the cartridge 100 and covers the staple openings 106 to retain the staples 152 prior to use of the cartridge 100. The staple pushers 160 interface with the staples 152 and slidingly interface with the cartridge body 158. Motion of the drive member 144 along the lead screw 134 results in engagement of the staple pushers 160 by distally-facing ramp surfaces 176 of the drive member 144 to drive the staple pushers 160 up relative to the cartridge body 158 to deploy the staples 152 as the drive member 144 moves towards the distal end 104. The knife member 146 includes proximal protrusions 168 and distal protrusions 170. The cover 166 is attached to the cartridge body 158.

Figure 11A:
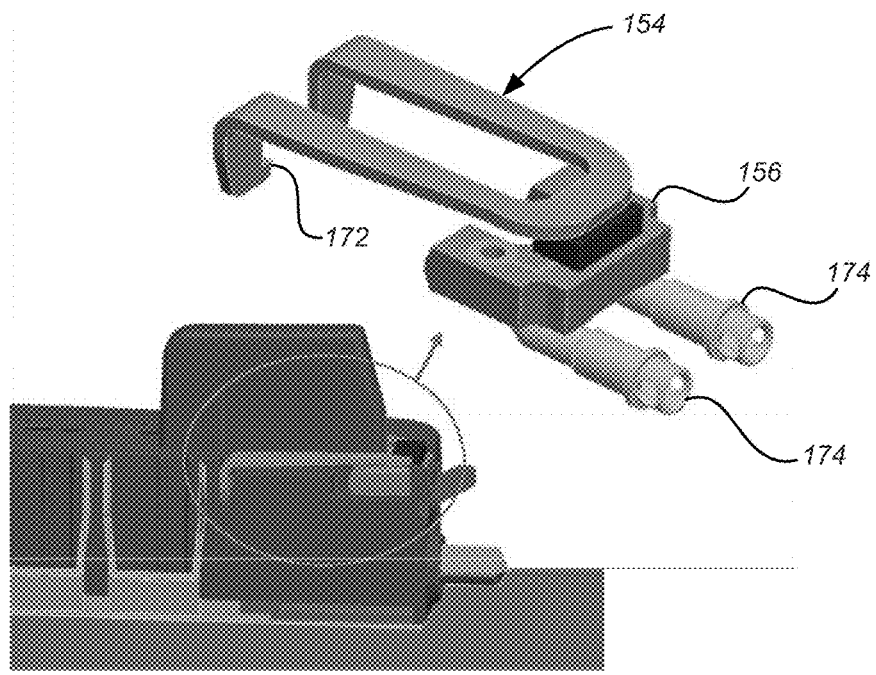
FIGS. 11A and 11B are perspective views illustrating a printed circuit assembly of the cartridge of FIG. 7.
Figure 11B:
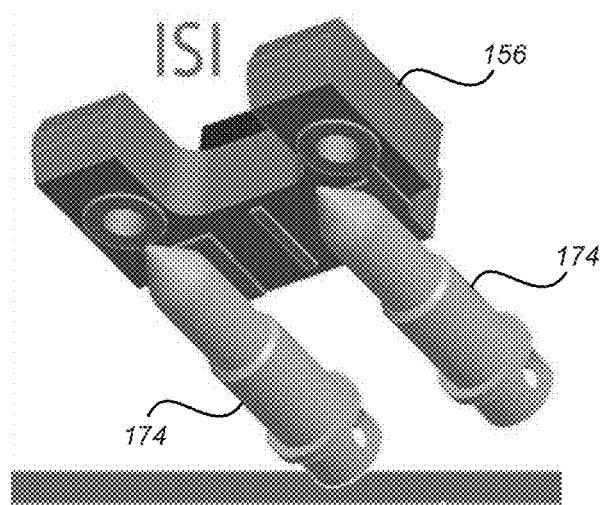

FIGS. 11A and 11B further illustrate the PCA 156 and the PCA spring 154. The PCA spring 154 interfaces with the cartridge body 158 and retains the PCA 156. The PCA spring 154 includes PCA spring hooks 172, which latch onto the cartridge body 158 to retain the PCA spring 154. When the cartridge 100 is attached to the end effector 118, instrument pins 174 of the end effector 118 slide beneath and lift the PCA 156, thereby electrically connecting the PCA 156 with the instrument pins 174 and allowing for the use of increased associated tolerances. This arrangement however is not critical, as long as the instrument pins 174 make suitable contact with the PCA 156. Accordingly, in some embodiments, the PCA 156 can be turned on edge such that the shown chip is out of the load path. The PCA 156 can be used to electronically store identification, configuration, and/or use information associated with the cartridge 100.

The cartridge 100 can be assembled using the following assembly sequence. First, with the cartridge body 158 in a "bottom up" orientation, the staple pushers 160 are installed into the staple openings 106. Next, the knife member 146 is installed into the proximal garage 110 with proximal protrusions 168 of the knife member 146 placed into proximal receptacles in the cartridge body 158. Next, the drive member 144, the thrust washer 162, and the lead screw nut 164 are installed onto the lead screw 134 and the lead screw nut 134 is laser welded flush to the end of the lead screw 134. The resulting lead screw assembly is then installed into the cartridge body 158 with the drive member 144 positioned at the proximal end of the lead screw 134. Next, the cover 166 is installed onto the cartridge body 158. The resulting assembly can then be lubricated, for example, by immersing the resulting assembly into a lubricant. Next, the assembly is flipped to a "top up" orientation and the PCA 156 is installed. Next, the PCA spring 154 is pushed onto the cartridge body 158 until the PCA spring hooks 172 latch. Next, the staples 152 are installed into the staple openings 106 and the retainer 116 is then installed. Finally, data is installed into the PCA 156.

Figure 12:
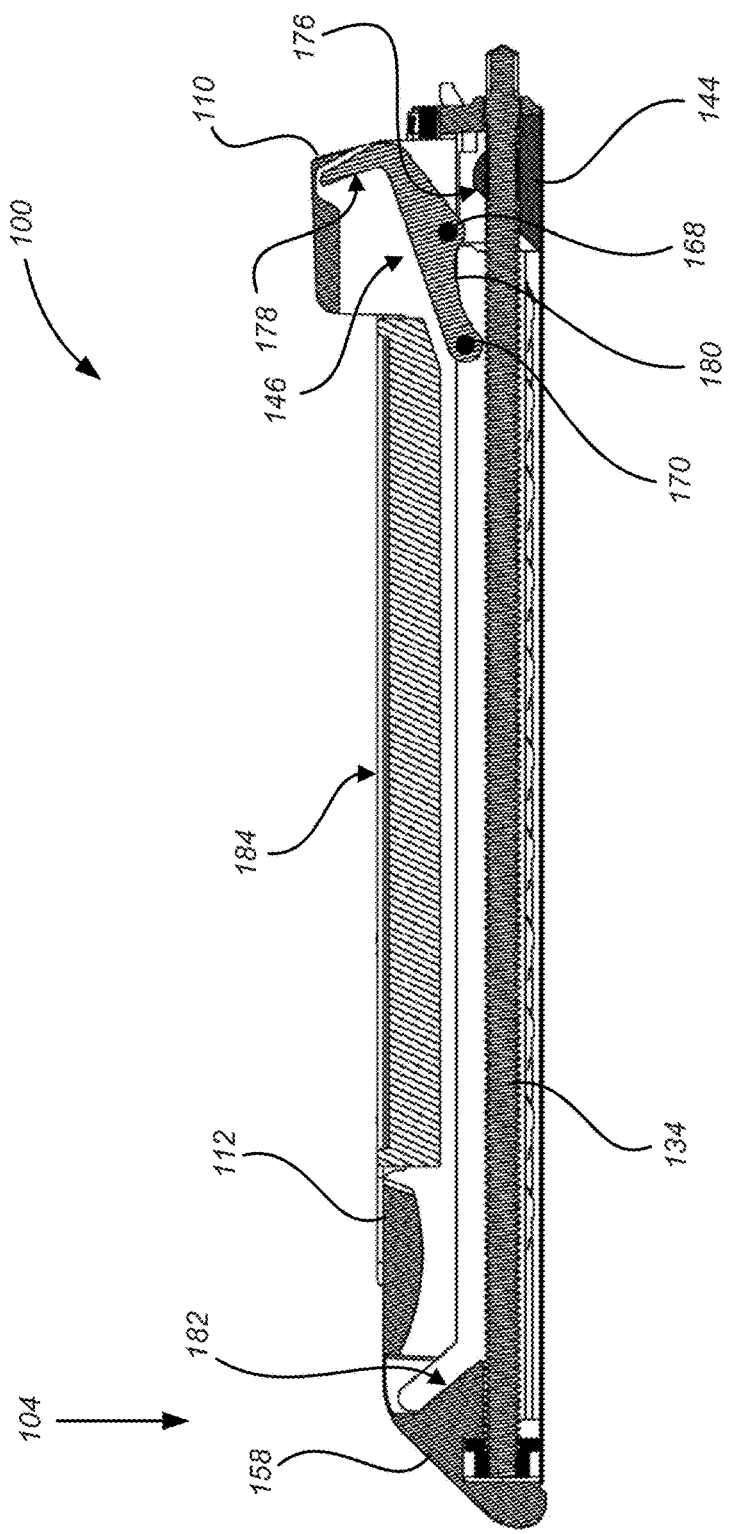
FIG. 12 is a cross-sectional view of a demountably attachable cartridge of a linear stapling and cutting surgical instrument, in accordance with many embodiments.

FIG. 12 illustrates components of the cartridge 100 related to the actuation of the knife member 146 from a starting position (illustrated) in which the knife member 146 is shielded by the proximal garage 110 to an ending position (not illustrated) in which the knife member 146 is shielded by the distal garage 112. The lead screw 134 is mounted for rotation relative to the cartridge body 158 and extends along the length of the cartridge body 158. The drive member 144 is internally threaded and is coupled with the lead screw 134 and slidably mounted in the cartridge body 158 for translation along the lead screw 134 in response to rotation of the lead screw 134. The drive member 144 includes one or more distally-facing ramps 176 configured to engage the staple pushers 160 as the drive member 144 is advanced toward the distal end 104 of the cartridge body 100. The knife member 146 includes a cutting blade 178, the body portion 180, the proximal protrusions 168 extending from opposite sides of the body portion 180, and the proximal protrusions 170 also extending from opposite sides of the body portion 180. As will be described in more detail below, when the drive member 144 is advanced distally from its illustrated starting position, the knife member 146 remains stationary relative to the cartridge body 158 until the drive member 144 contacts the distal protrusions 170 by which the knife member 146 is then driven distally by the drive member 144. Near the end of the distal travel of the drive member 144, the distal end of the knife member 146 is driven along a cam surface 182 of the cartridge body 158, thereby raising the distal end of the knife member 146 to lower the cutting blade 178 below an upper surface 184 of the cartridge body 158 and into the distal garage 112. The knife member body portion 180 is constrained by opposing surfaces of the cartridge body 158 that define the longitudinal slot 108. The knife proximal and distal protrusions 168, 170 extend from opposite sides of the knife member body portion 180 beyond the width of the longitudinal slot 108, thereby serving to constrain the knife member 146 vertically relative to the cartridge body 158 and the drive member 144.

Figure 13A:
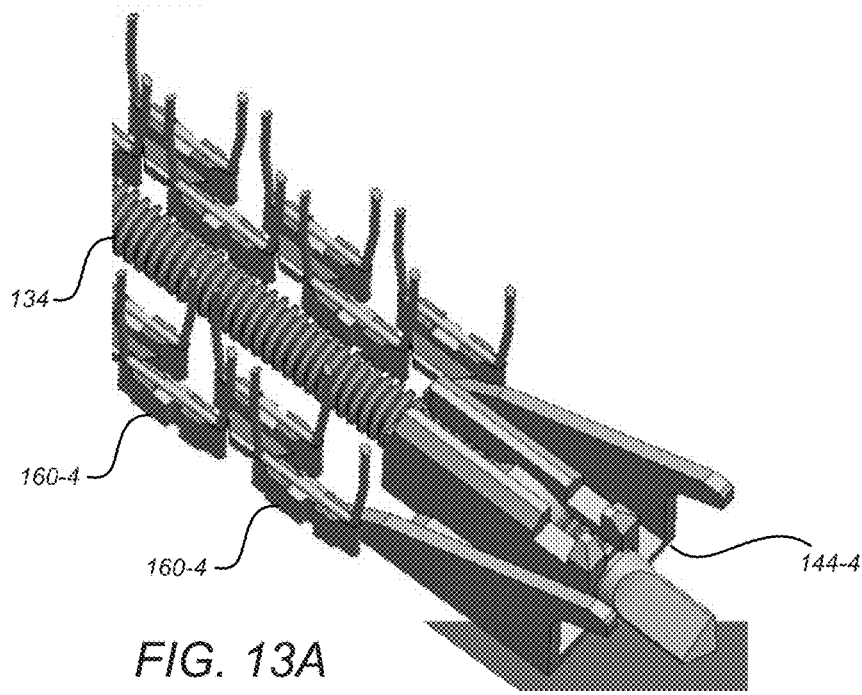
FIG. 13A is a partial perspective view of staple deployment related components of a demountably attachable cartridge of a linear stapling and cutting surgical instrument having four rows of staples, in accordance with many embodiments.
Figure 13B:
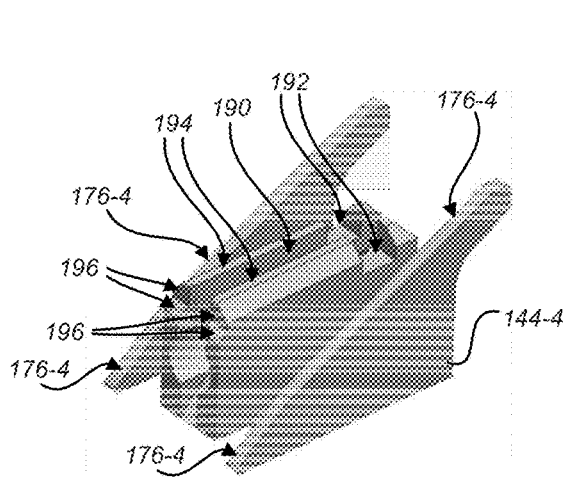
FIG. 13B is a perspective view of a drive member of the cartridge of FIG. 13A.
Figure 13C:
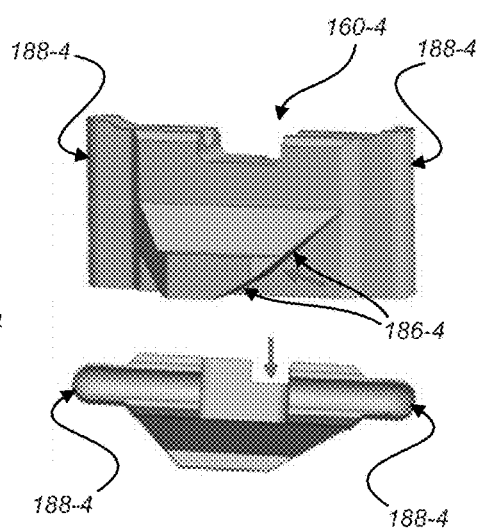
FIG. 13C includes perspective views of a staple pusher of the cartridge of FIG. 13A.

FIGS. 13A through 13C show staple deployment related components of a linear stapling and cutting surgical instrument having four rows of staples, in accordance with many embodiments. Similar to the cartridge 100, an internally-threaded drive member 144-4 is coupled with a lead screw 134 and slidably mounted in a cartridge body (not shown) for translation along the lead screw 134 in response to rotation of the lead screw 134. The drive member 144-4 includes distally facing bi-linear ramps 176-4, which engage staple pushers 160-4 as the drive member 144-4 is advanced distally along the lead screw 134. Each of the staple pushers 160-4 is configured to push a single staple (not shown). Each of the staple pushers 160-4 has bi-linear ramp surfaces 186-6, which are configured to interface with the correspondingly sloped bi-linear ramps 176-4 of the drive member 144-4. Each of the staple pushers 160-4 has end portions 188-4 that are shaped to slidingly interface with staple openings in the cartridge body.

The drive member 144-4 is configured to accommodate and interface with the knife member 146 to initially move distally relative to the knife member 146, then drive the knife member 146 toward the distal end of the cartridge body and push the distal end of the knife member 146 up the distal ramp 182 of the cartridge body 158. The drive member 144-4 features that interface with the knife member 146 include a central slot 190, proximal receptacles 192, top surfaces 194, and distal surfaces 196. The central slot 190 accommodates the knife body portion 180 throughout the stroke of the knife member 146 from its starting position in the proximal garage 110 to its ending position in the distal garage 112. The proximal receptacles 192 accommodate the knife member proximal protrusions 168 while the knife member 146 is driven distally by the drive member 144-4. The top surfaces 194 interface with the proximal protrusions 168 to secure engagement between the proximal protrusions 168 and receptacles in the cartridge body 158 during the initial distal movement of the drive member 144-4 in which the drive member 144-4 is moved distally relative to both the cartridge body 158 and the knife member 146 and the knife member 146 is held stationary relative to the cartridge body 158 via the engagement between the proximal protrusions 168 and the associated cartridge body receptacles. After the initial relative distal movement of the drive member 144-4 relative to the knife member 146, the drive member distal surfaces 196 interface with the knife member distal protrusions 170 to drive the knife member 146 distally and, in conjunction with surfaces of the cartridge body 158 on both sides of the longitudinal slot 108, control the vertical position of the distal protrusions 170 as the knife member 146 is driven distally. When the distal portion of the knife member 146 is driven up the cam surface 182, the distal protrusions 170 separate from the distal surfaces 196 and the knife member 146 is then driven by a proximal wall of the drive member proximal receptacles 192, which interface with the knife member proximal protrusions 168 to drive the knife member 146 along the cam surface 182, thereby stowing the cutting blade 178 into the distal garage 112.

Figure 14A:
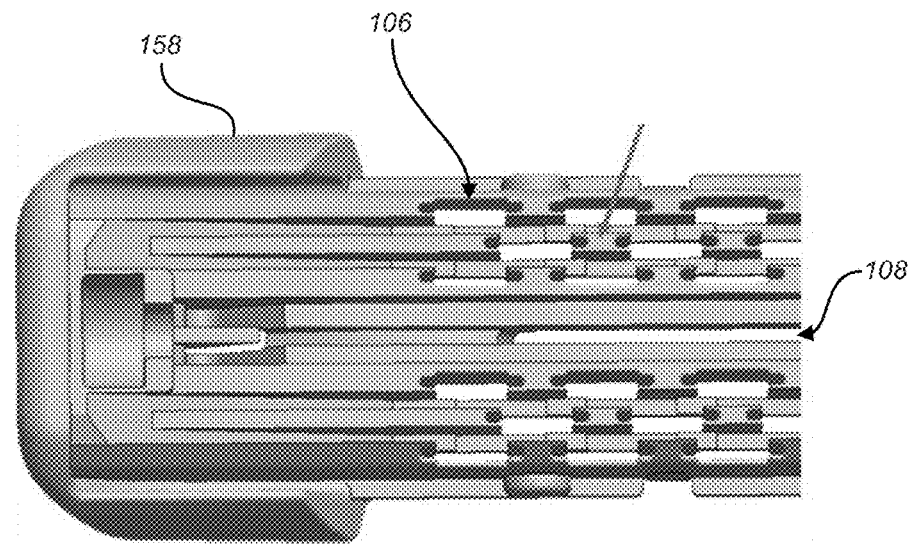
FIG. 14A shows a distal end of a housing of the cartridge of FIG. 7.
Figure 14B:
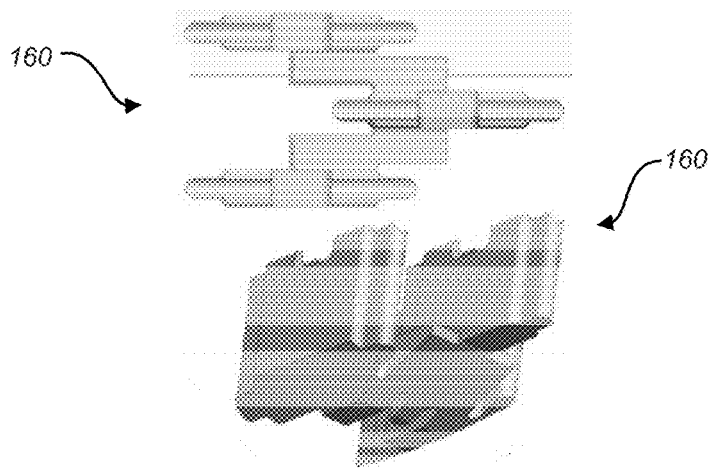
FIG. 14B includes perspective views of a staple pusher of the cartridge of FIG. 7.

FIG. 14A shows a distal end of the cartridge body 158. FIG. 14B shows a top view and a perspective view of one of the staple pushers 160. As illustrated, the staple openings 106 and the staple pushers 160 have complementary shapes such that each of the staple pushers 160 is accommodated within one of the staple openings 106 for translation within the staple opening 106 in response to being driven by the drive member 144 as the drive member 144 is translated toward the cartridge distal end 104.

Figure 14C:
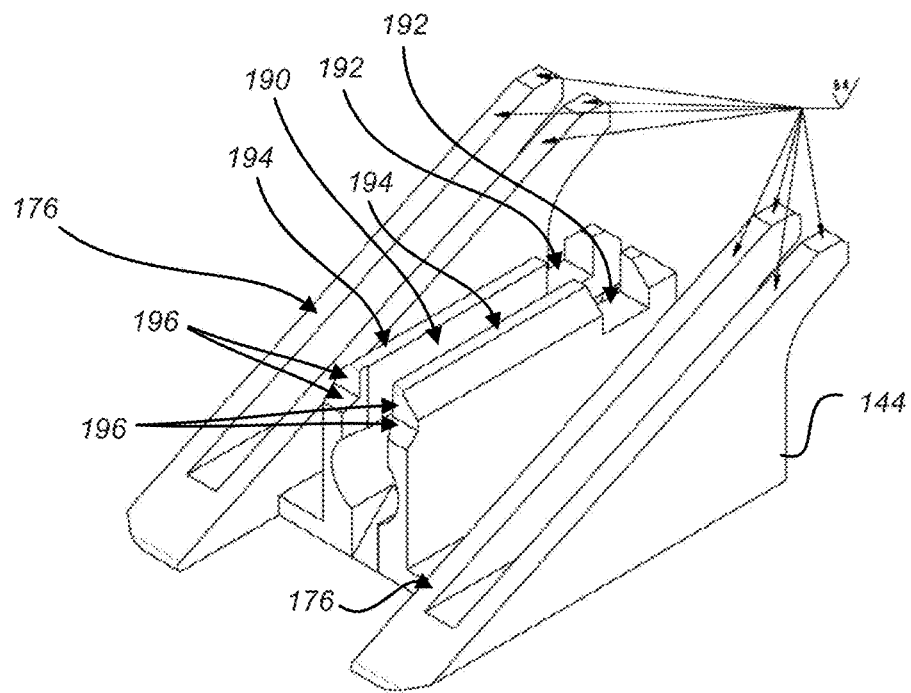
FIG. 14C is a perspective view of a drive member of the cartridge of FIG. 7.
Figure 14D:
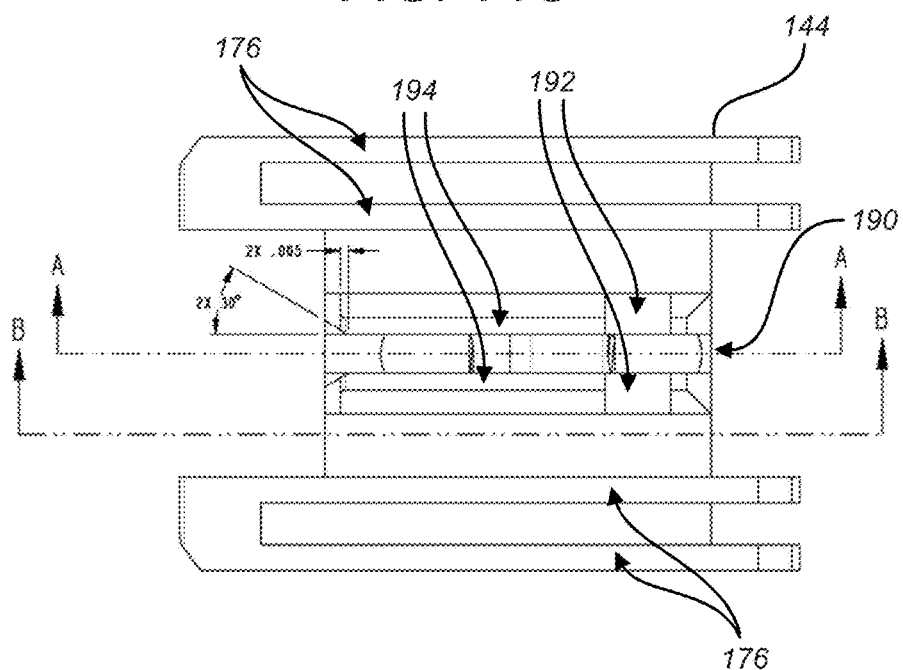
FIG. 14D is a plan view of the drive member of the cartridge of FIG. 7.
Figure 14E:
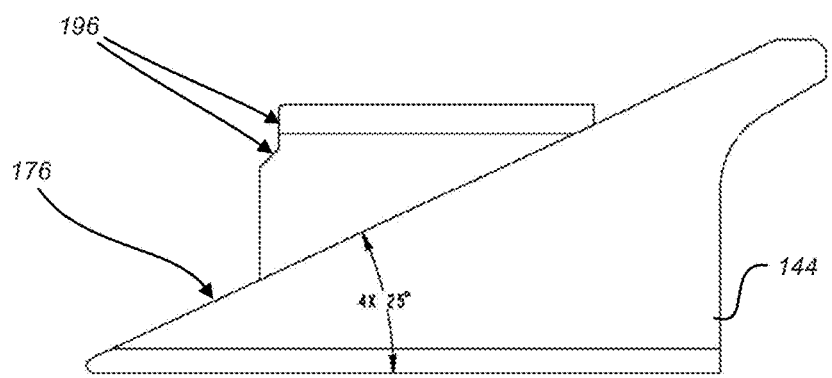
FIG. 14E is a side view of the drive member of the cartridge of FIG. 7.
Figure 14F:
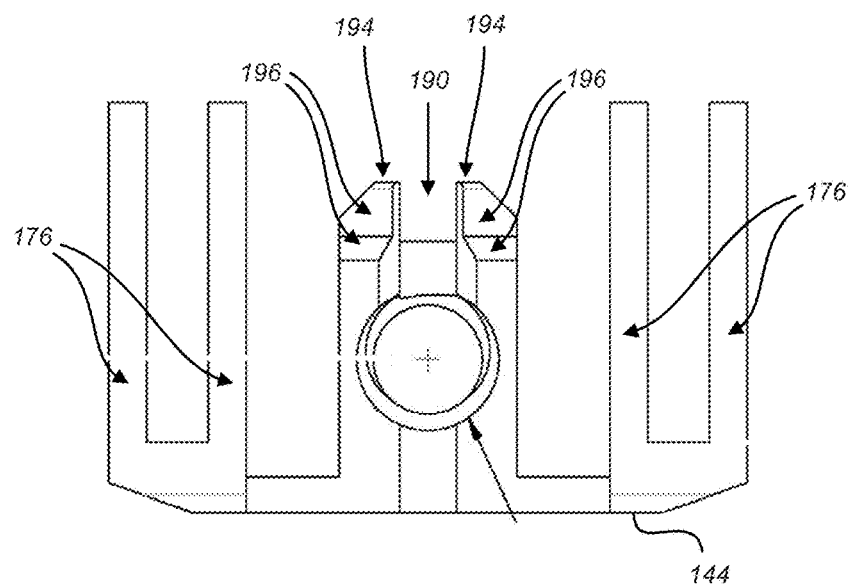
FIG. 14F is a distal end view of the drive member of the cartridge of FIG. 7.
Figure 14G:
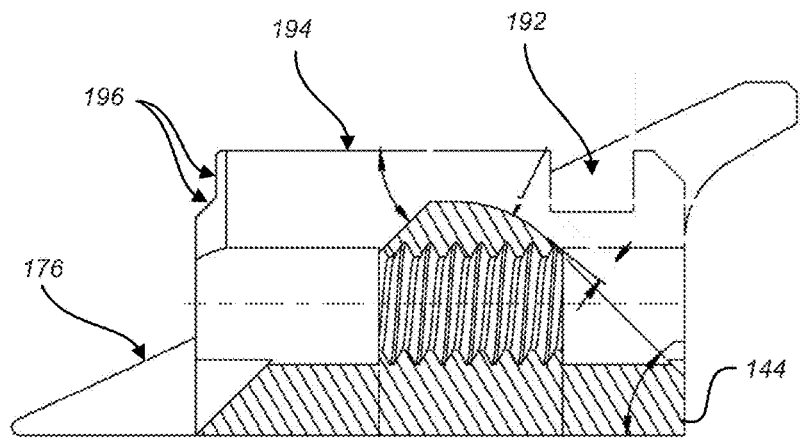
FIG. 14G shows cross section AA of the drive member of the cartridge of FIG. 7 as defined in FIG. 14D.
Figure 14H:
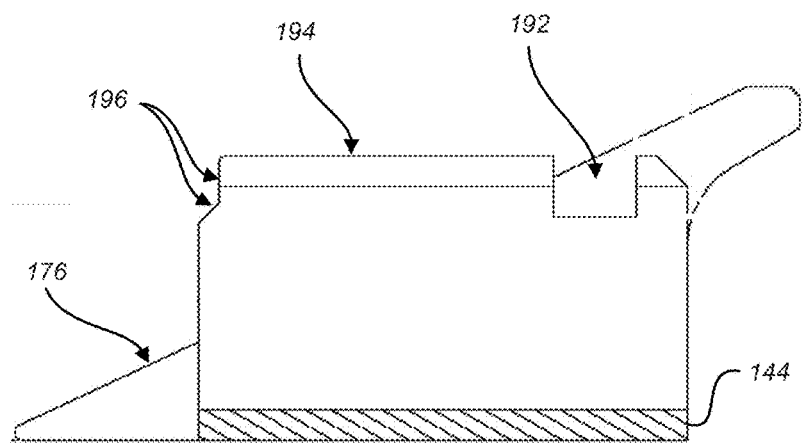
FIG. 14H shows cross section BB of the drive member of the cartridge of FIG. 7 as defined in FIG. 14D.

FIGS. 14C through 14H provide additional illustration of the drive member 144. FIG. 14C shows a perspective view of the drive member 144. FIG. 14D shows a top view of the drive member 144. FIG. 14E shows a side view of the drive member 144. FIG. 14F shows a distal end view of the drive member 144. FIG. 14G shows cross-sectional view AA as defined in FIG. 14D. And FIG. 14H shows cross-sectional view BB as defined in FIG. 14D.

FIGS. 15A through 15C provide additional illustration of the knife member 146. In many embodiments, the cutting blade 178 is formed integral to the knife member body portion 180. The proximal protrusions 168 and the distal protrusions 170 can be integral with the knife member body portion 180, or formed by press-fitting pins into transverse holes in the knife-member body portion 180. The body portion 180 and the pins can be formed from a suitable material(s), for example, 17-4 PH, 440A, 420 or 465 stainless steels.

The cutting blade 178 is beveled to a ground edge on both sides, but can be flat with a ground edge, or beveled only on one side while ground on the other. Additional honing can be performed to create multiple angles on each side of the cutting blade 178.

The configuration of the knife member 146 provides robust support of the cutting blade 178, which may be particularly advantageous when the cutting blade 178 is used to cut through something other than soft tissue. For example, it may occur that the cartridge 100 is used to deploy staples through previously stapled tissue, thereby possibly placing an existing staple in the path of the cutting blade 178 so that the existing staple must be cut <or dragged> by the cutting blade 178.

Figure 15D:
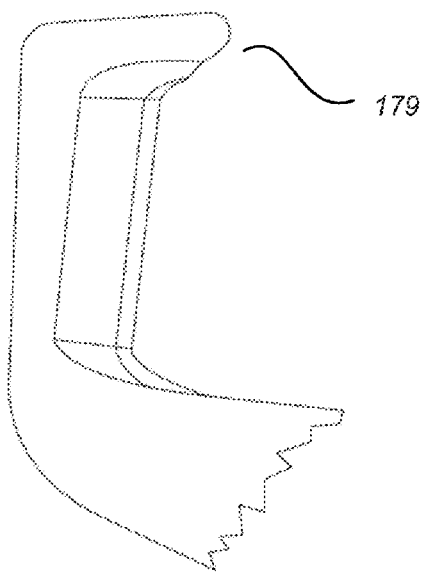
FIGS. 15D through 15G respectively show partial side views of knife members, in accordance with many embodiments.

FIG. 15D illustrates an alternative configuration of the knife member 146. In many embodiments, the knife member has a cutting blade 178 with a hooked tip 179. The hooked tip is blunted and protrudes well distally past, and well laterally above, the top-most cutting edge of the cutting blade. The hooked tip 179 can help ensure that a full thickness of tissue is cut by preventing tissue from climbing over the height of the cutting blade 178. The hooked tip can also reduce the risk of injury to operating room staff in case a device failure leaves the cutting blade 178 exposed.

Figure 15E:
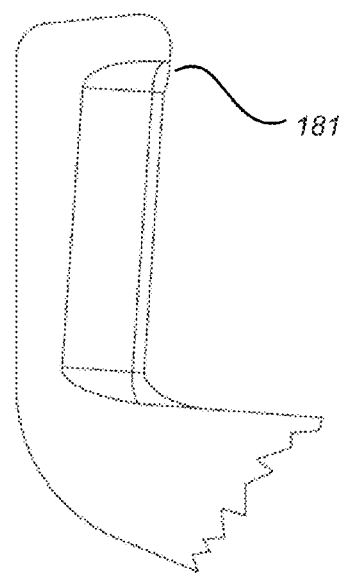

FIG. 15E illustrates another alternative configuration of the knife member 146. In many embodiments, the knife member has a cutting blade 178 with a blunted tip 181. The blunted tip protrudes slightly distally past (or is collinear with), but well laterally above, the top-most cutting edge of the cutting blade 179. Like the hooked tip 179 of the cutting blade 178 of FIG. 15D, the blunted tip 181 of cutting blade 179 can help prevent tissue climb-over and reduce risk of accidental injury.

Figure 15F:
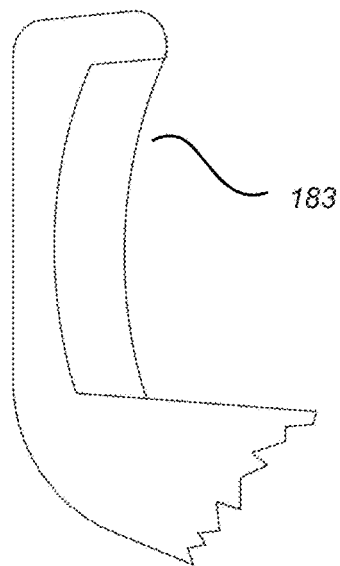

FIG. 15F illustrates another alternative configuration of the knife member 146. In many embodiments, the knife member has a curved cutting blade 183 with a blunted tip. The blunted tip protrudes slightly distally past (or is collinear with), but well laterally above, the top-most cutting edge of the cutting blade 183. The blunted tip of curved cutting blade 183 can help prevent tissue climb-over and reduce risk of accidental injury. The curved cutting blade 183 can also help further that purpose by gathering and centering tissue within its center-most portion. This can also help prevent tissue from clogging the lower-most blade/cartridge interface via the centering action. The cutting blade 183 is beveled to a ground edge on both sides, but can be flat with a ground edge, or beveled only on one side while ground on the other. Additional honing can be performed to create multiple angles on each side of the cutting blade 183.

Figure 15G:
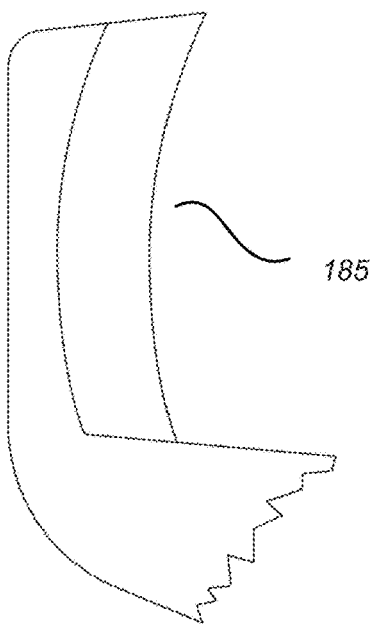

FIG. 15G illustrates another alternative configuration of the knife member 146. In many embodiments, the knife member has a curved cutting blade 185, which is largely identical to the curved cutting blade 183 of FIG. 15F, and thus shares the same features. However, the curved cutting blade 185 does not include a blunted tip, since in some applications the curvature of the cutting blade 185 alone can prevent tissue from climbing-over.

Figure 15H:
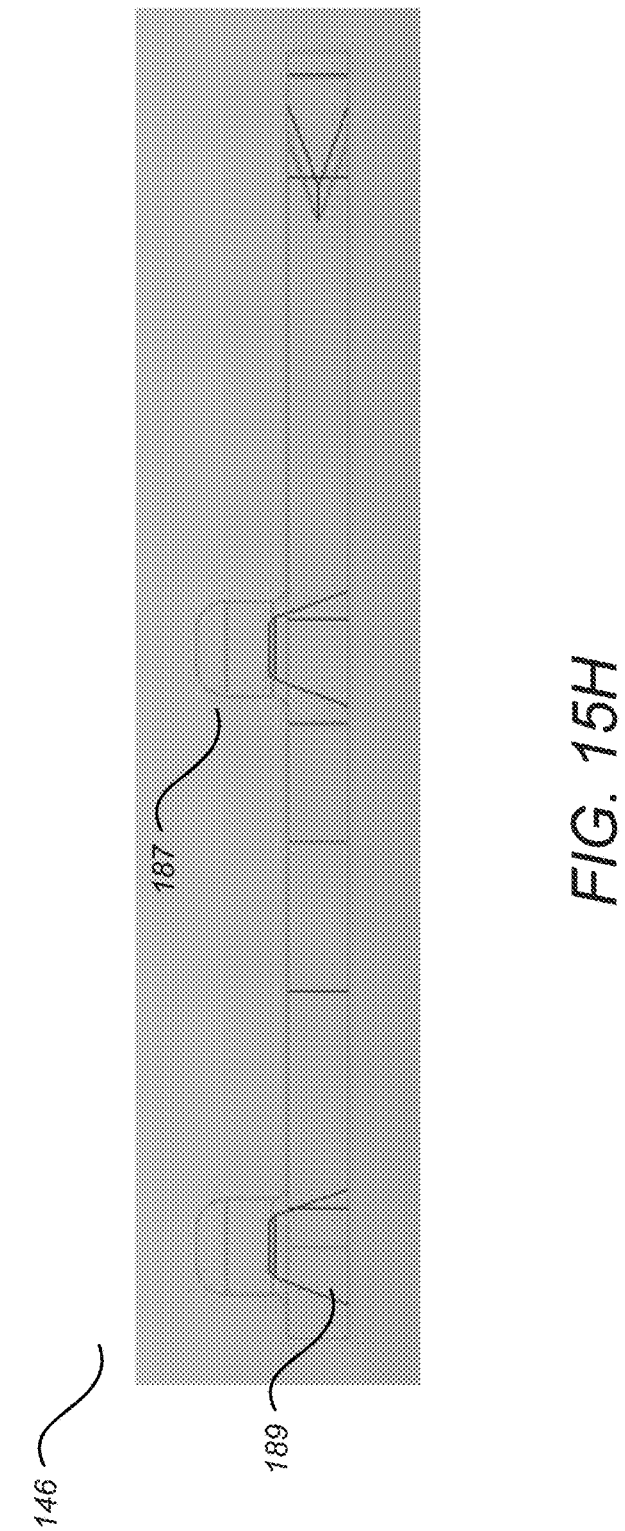
FIG. 15H shows a top view of knife member, in accordance with many embodiments.

FIG. 15H illustrates another alternative configuration of the knife member 146. Here, the knife member 146 is formed with integral pins 187 extending laterally on one side. The pins 187 respectively provide male coupling surfaces for attaching the knife member 146 to other portions of the cartridge 100 in a similar manner to pins 168 and 170 of FIG. 15C. The pins 187 can be formed, for example, by: stamping a singular piece of source material to form the knife member 146 integrally with the pins 187; welding/pressing/bonding the pins 187 into a separate knife member 146; or by molding (with additional forging as needed) the knife member 146 integrally with the pins 187. The pins 187 can also extend from both sides of the knife member 146, on the side opposite as shown, or the pins can extend from each side of the knife member 146 at different or the same proximal and distal portions of the knife member 146. Indented surfaces 189 forming blind holes may also be formed opposite the pins by the above processes or later machined into the knife member. The indented surfaces 189 respectively provide female coupling surfaces for attaching the knife member 146 to other portions of the cartridge 100. It should be understood that this pin configuration can apply to any of the blade designs disclosed herein.

Figure 16A:
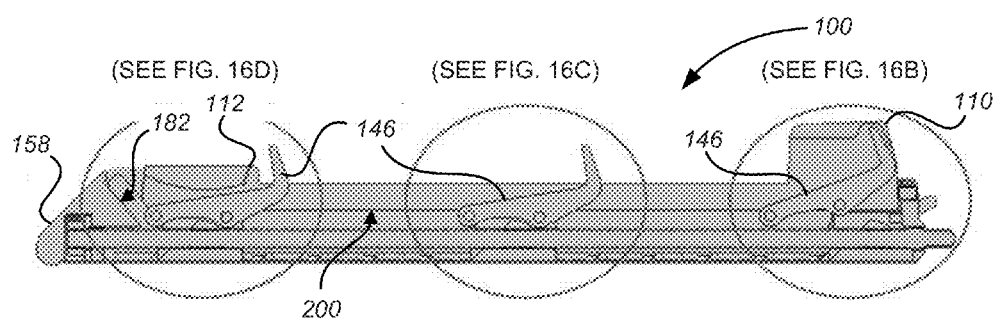
FIG. 16A illustrates the actuation of the knife member of the cartridge of FIG. 7.

FIGS. 16A through 16D illustrate the interaction of components of the cartridge 100 during the actuation of the knife member 146 from its starting position in the proximal garage 110 to its final position in the distal garage 112. FIG. 16A shows three different positions of the knife member 146 relative to the cartridge body 158, specifically a starting proximal-most position, an intermediate position, and a distal position just before the distal end of the knife member 146 is driven up the cartridge body cam surface 182.

Figure 16B:
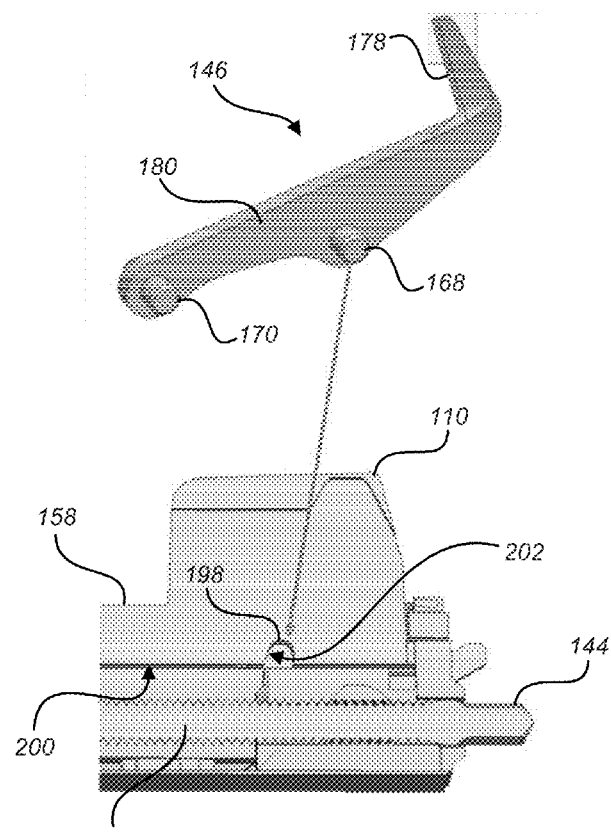
FIG. 16B shows a housing receptacle that receives a protrusion of the knife member to restrain the knife member from moving distally during a movement of the drive member distally, in accordance with many embodiments.

As shown in FIGS. 16A and 16B, in the starting proximal-most position, the drive member 144 is positioned at the proximal end of the lead screw 134 and the knife member proximal protrusions 168 are disposed within receptacles 198 in the cartridge body 158. The drive member upper surfaces 194 interface with the knife member proximal protrusions 168 to retain the proximal protrusions 168 in the cartridge body receptacles 198, thereby securing engagement between the proximal protrusions 168 and the cartridge body receptacles 198. The knife member distal protrusions 170 and the distal end of the knife are trapped between a central cavity ceiling 200 of the cartridge body 158 and the lead screw 134 and the knife member body portion 180 is disposed within the longitudinal slot 108, thereby restraining the knife member 146 in a substantially fixed position and orientation relative to the cartridge body 158.

From the starting proximal-most position, rotation of the lead screw 134 drives the drive member 144 distally along the lead screw 134. Throughout a starting "lost-motion" portion of the distal motion of the drive member 144 along the lead screw 134, the proximal protrusions 168 remain trapped in the cartridge body receptacles 198 by the drive member upper surfaces 194. When the drive member 144 has moved distally to a point where the drive member distal surfaces 196 contact the knife member distal protrusions 170, the drive member proximal receptacles 192 are disposed below the cartridge body receptacles 198, thereby permitting the knife member 146 to rotate to transfer the proximal protrusions 168 from the cartridge body receptacles 198 to the drive member proximal receptacles 192. To facilitate this transfer, a distal surface 202 of the cartridge body receptacles 198 is sloped as illustrated to enhance the transfer by imparting a downward force component on the proximal protrusions 168 as the knife member distal surfaces 196 drive the knife member 146 distally via contact with the knife member distal protrusions 170.

Figure 16C:
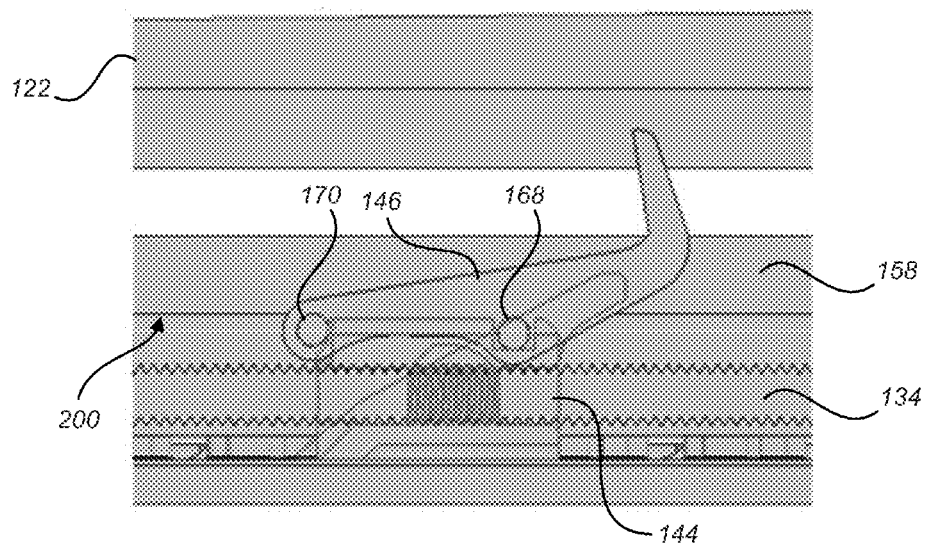
FIG. 16C shows the knife member coupled with the drive member while the drive member drives the knife member distally, in accordance with many embodiments.

FIG. 16C illustrates interaction between the drive member 144, the knife member 146, and the cartridge body 158 following the "lost motion" portion of the distal motion of the drive member 144 along the lead screw 134. After the drive member distal surfaces 196 come into contact with the knife member distal protrusions 170 causing the knife member 146 to rotate to transfer the proximal protrusions 168 into the drive member proximal receptacles 192, continued rotation of the lead screw 134 results in continued distal motion of the drive member 144 and corresponding distal motion of the knife member 146. During this continued distal motion, the knife member 146 is constrained by both the drive member distal protrusions 170 interaction with the ceiling 200 of the cartridge body 158 and the knife member body portion 180 interaction within the longitudinal slot 108 of the cartridge body 158.

Figure 16D:
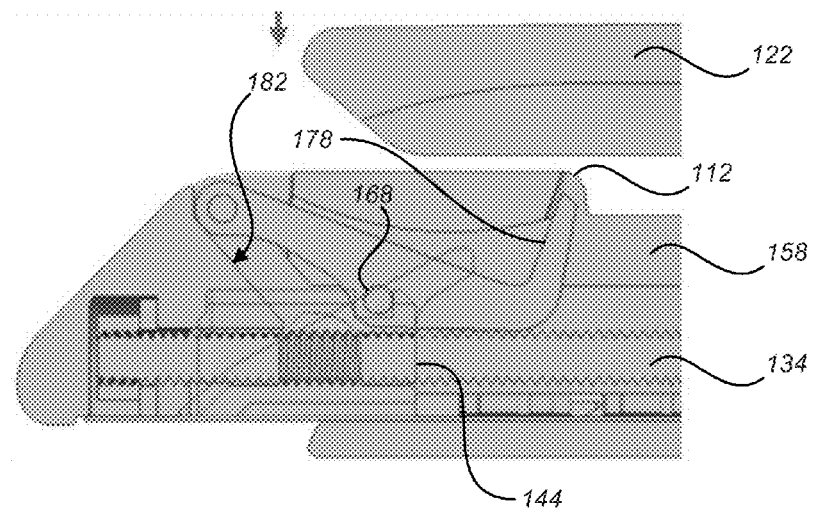
FIG. 16D shows the knife member at the end of the actuation stroke after the distal end of the knife member has been driven along a cam surface of the housing to raise the distal end of the knife to lower the cutting blade of the knife into the housing, in accordance with many embodiments.

FIGS. 16A and 16D illustrate interaction between the drive member 144, the knife member 146, and the cartridge body 158 (particularly the cam surface 182 of the cartridge body 158) during a terminal portion of the distal motion of the drive member 144 along the lead screw 134. As the drive member 144 is advanced distally near the end of its travel along the lead screw 134, the distal end of the knife member 146 comes into contact with the cam surface 182 and is subsequently driven along the cam surface 182 until reaching the ending distal-most position illustrated in FIG. 16D in which the drive member 144 has reached the end of its travel along the lead screw 134. As a result of the distal end of the knife member 146 being driven along the upward sloping cam surface 182, the knife member 146 rotates approximately around the knife member proximal protrusions 168, thereby lowering the cutting blade 178 into the distal garage 112.

Figure 16E:
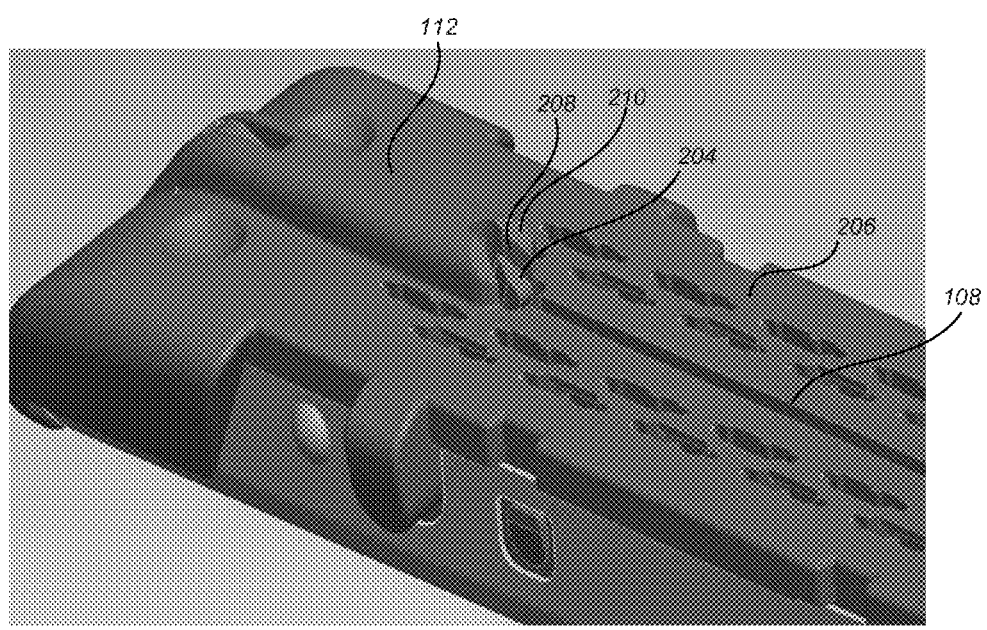
FIG. 16E shows the knife member in a predetermined parked position of the distal garage, in accordance with many embodiments.

FIG. 16E illustrates the relationship between the knife member 146 and the cartridge body 158, after the reaching the ending distal-most position illustrated in FIG. 16D. At the distal-most position, the knife member 146 is moved by the drive member 144 into a predetermined parked position within the distal garage 112. In that position, a lower portion of the knife member 146 is unexposed within the cartridge body 158, while an upper portion 204 that includes the tip remains displaced above upper surface 206. However, all cutting edges of the upper portion of the knife member 146 are laterally protected from accidental touching by the distal garage 112.

The distal garage has lateral surfaces 208, here forming a notch, that prevent users from inadvertent cuts when removing the cartridge 100 or otherwise handling the cartridge 100. This is accomplished by surrounding all cutting edges of the upper portion 204 with lateral surfaces 208 of the distal garage 112. Additionally, the lateral surfaces 208 of the garage 112 that face the upper portion of the knife member 146 are spaced far enough (more than the maximum diameter of the staple wire e.g., 0.25 mm) from the knife member 146 to accommodate a dislodged staple in between. Additional spacing is provided in the distal-most portion of the lateral surfaces, which causes the lateral surfaces to resemble a key pattern when viewed from above. The additional distal spacing, here being circular, allows for a pinched diameter of a staple that becomes lodged between the knife member 146 and the lateral surfaces 208 (and thus forcibly pinched as the knife member is brought fully into the predetermined parked position). In this manner, a dislodged staple can "wrap" around the knife member 146.

As shown, the lateral surfaces 208 of the distal garage 112 can diverge at an angle ranging from 25-45° to form a V or U shaped notch. The diverging lateral surfaces 208 are spaced apart wider, with respect to the longitudinal slot 108, at their proximal-most gap as compared to the more distal locations. This gap allows cutting edge of the knife member 146 to apply significant bending force to a staple that bridges the proximal-most gap as the staple is brought into contact with the proximal-most gap by the knife member 146, whereas a lesser gap may result in a jam. Accordingly, if a staple is caught and dragged into the garage, there is enough lateral clearance between the upper portion of the knife member 146 and the lateral surfaces 208 to accommodate the section width of the staple while allowing the knife member 146 to fully engage into the predetermined parked position. Thus, if a staple becomes lodged in this manner, user safety is not compromised by an exposed cutting edge.

The distal garage 112 also includes at least one staple ejecting surface 210. Here, the staple ejecting surface 210 is formed as symmetrical ramped surfaces that are transverse to the lateral surfaces 208, resembling a chamfer. An imaginary planar extension of the staple ejecting surface 210 is non-parallel with the upper surface 206 of the cartridge body and forms an angle with respect to the upper surface 206 ranging from 30-60°. In use, the staple ejecting surface can cause a captured staple to move upwardly along the cutting edge of the knife member 146 as the knife member 146 is moved distally, thus, in some cases ejecting the staple as the staple is pushed over the top of the knife member 146.

Linear Stapling and Cutting Methods

Figure 17:
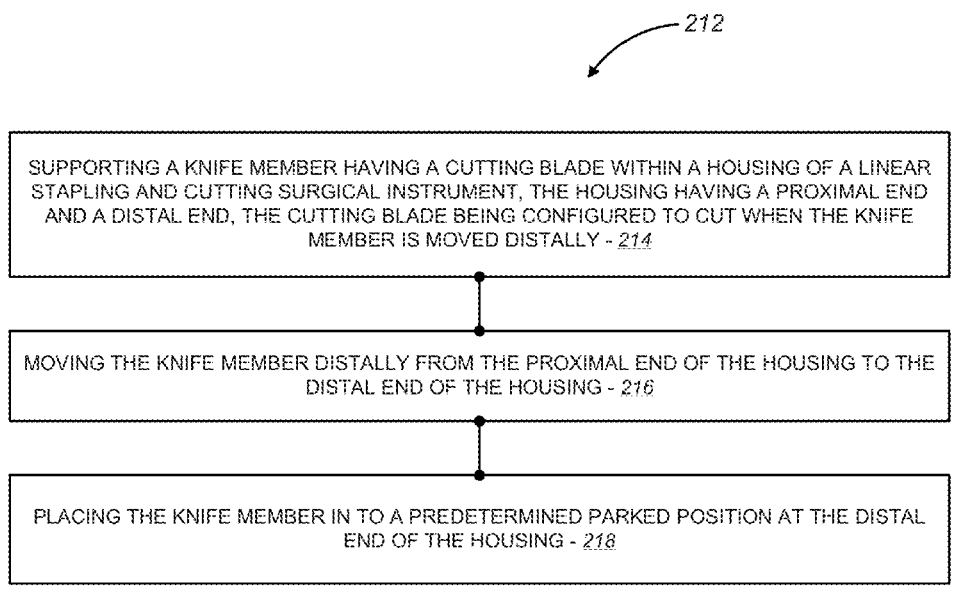
FIG. 17 lists acts of a method of deploying staples from and of articulating a cutting blade in a linear stapling and cutting surgical instrument, in accordance with many embodiments.

FIG. 17 shows acts of a method 212 for deploying stables from, and of articulating a cutting blade in, a linear stapling and cutting surgical instrument, in accordance with many embodiments. Any suitable linear stapling and cutting surgical instrument can be used to practice the method 212. For example, the linear stapling and cutting surgical instruments and cartridges described herein can be used to practice the method 212.

At act 214, a knife member having a cutting blade is supported within a housing of a linear stapling and cutting surgical instrument. The housing has a proximal end and a distal end. The cutting blade is configured to cut when the knife member is moved distally.

In act 216, a drive member is moved distally from the proximal end of the housing to the distal end of the housing such that the cutting blade becomes exposed. During movement of the knife member, a plurality of staples exits the upper surface.

In act 218, the knife member is placed into a predetermined parked position at the distal end of the housing. In this position, a first portion of the cutting blade is made to displace below the upper surface. A second portion of the cutting blade remains above the upper surface, but is laterally faced by a garage that extends above the upper surface. There is enough lateral clearance in the predetermined parked position to accommodate a dislodged staple that may be forcibly placed between the knife member and the lateral surfaces.

The methods disclosed herein can be employed in any suitable application. For example, the methods disclosed herein can be employed in surgical instruments, manual or powered, hand-held or robotic, directly controlled or teleoperated, for open or minimally invasive (single or multiport) procedures.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical instrument comprising:
an elongated shaft having a shaft distal end and a shaft proximal end;
an end effector coupled to the shaft distal end and including opposed jaws;
a knife member having a cutting blade configured to cut when the knife member is moved distally toward a predetermined parked position; and
a housing included in one of the jaws; the housing including:
a planar upper surface having a plurality of staple openings extending through the planar upper surface, each of the staple opening being configured to accommodate and guide a respective staple during ejection of the staple in an upward direction relative to the planar upper surface;
a longitudinal slot accommodating distal movement of the knife member and through which a portion of the cutting blade extends beyond the planar upper surface during a cutting motion of the knife member; and
a distal garage configured to accommodate the knife member in the predetermined parked position; the distal garage including a pair lateral surfaces between which an exposed portion of the cutting blade that protrudes beyond the planar upper surface when the knife member is in the predetermined parked position is disposed; each of the pair of lateral surfaces being oriented transverse to the planar upper surface, extending in the upward direction relative to the planar upper surface, and offset from the exposed portion of the cutting blade by more than 0.25 mm.

2. The surgical instrument of claim 1, wherein the pair of lateral surfaces at least partially define a notch in the distal garage sized to accommodate the exposed portion of the cutting blade and a dislodged staple wrapped around the exposed portion of the cutting blade when the knife member is in the predetermined parked position, the dislodges staple having a wire diameter of up to 0.25 mm.

3. The surgical instrument of claim 1, wherein the knife member is moveable into the predetermined parked position via translation and rotation of the knife member such that a portion of the cutting blade displaces below the planar upper surface and the exposed portion of the cutting blade remains above the planar upper surface.

4. The surgical instrument of claim 1, wherein the garage includes at least one staple ejecting surface configured to engage a dislodged staple wrapped around the cutting blade and cause the dislodged staple to move along the cutting blade away from the planar upper surface as the knife member is moved toward the predetermined parked position.

5. The surgical instrument of claim 4, wherein the at least one staple ejecting surface is transverse each of the pair of lateral surfaces.

6. The surgical instrument of claim 4, wherein the at least one staple ejecting surface is non-parallel to the planar upper surface.

7. The surgical instrument of claim 6, wherein the at least one staple ejecting surface is at an angle ranging from 30-60° with respect to the planar upper surface.

8. The surgical instrument of claim 1, wherein the knife member is carried by a drive member.

9. The surgical instrument of claim 8, wherein in the predetermined parked position the drive member is fully displaced within the distal garage.

10. The surgical instrument of claim 1, wherein the pair of lateral surfaces diverge at an angle ranging from 25-45°.

11. A demountably attachable cartridge of a surgical instrument, the cartridge comprising:
a knife member having a cutting blade configured to cut when the knife member is moved distally toward a predetermined parked position; and
a housing included in one of the jaws and demountably attachable to an end effector of the surgical instrument, the housing including:
a planar upper surface having a plurality of staple openings extending through the planar upper surface, each of the staple opening being configured to accommodate and guide a respective staple during ejection of the staple in an upward direction relative to the planar upper surface;
a longitudinal slot accommodating distal movement of the knife member and through which a portion of the cutting blade extends beyond the planar upper surface during a cutting motion of the knife member; and
a distal garage configured to accommodate the knife member in the predetermined parked position; the distal garage including a pair lateral surfaces between which an exposed portion of the cutting blade that protrudes beyond the planar upper surface when the knife member is in the predetermined parked position is disposed; each of the pair of lateral surfaces being oriented transverse to the planar upper surface, extending in the upward direction relative to the planar upper surface, and offset from the exposed portion of the cutting blade by more than 0.25 mm.

12. The cartridge of claim 11, wherein the pair of lateral surfaces at least partially define a notch in the distal garage sized to accommodate the exposed portion of the cutting blade and a dislodged staple wrapped around the exposed portion of the cutting blade when the knife member is in the predetermined parked position, the dislodges staple having a wire diameter of up to 0.25 mm.

13. The cartridge of claim 11, wherein the knife member is moveable into the predetermined parked position via translation and rotation of the knife member such that a portion of the cutting blade displaces below the planar upper surface and the exposed portion of the cutting blade remains above the planar upper surface.

14. The cartridge of claim 1, wherein the garage includes at least one staple ejecting surface configured to engage a dislodged staple wrapped around the cutting blade and cause the dislodged staple to move along the cutting blade away from the planar upper surface as the knife member is moved toward the predetermined parked position.

15. The cartridge of claim 14, wherein the at least one staple ejecting surface is transverse each of the pair of lateral surfaces.

16. The cartridge of claim 14, wherein the at least one staple ejecting surface is non-parallel to the planar upper surface.

17. The cartridge of claim 16, wherein the at least one staple ejecting surface is at an angle ranging from 30-60° with respect to the planar upper surface.

18. The cartridge of claim 11, wherein the knife member is carried by a drive member.

19. The cartridge of claim 18, wherein in the predetermined parked position the drive member is fully displaced within the distal garage.

20. The cartridge of claim 11, wherein the pair of lateral surfaces diverge at an angle ranging from 25-45°.

* * * * *